(12) United States Patent
Klistorner et al.

(10) Patent No.: US 6,477,407 B1
(45) Date of Patent: Nov. 5, 2002

(54) ELECTROPHYSIOLOGICAL VISUAL FIELD MEASUREMENT

(75) Inventors: Alexander I. Klistorner, Sydney (AU); Stuart L. Graham, Sydney (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 09/700,249

(22) PCT Filed: May 7, 1999

(86) PCT No.: PCT/AU99/00340
§ 371 (c)(1),
(2), (4) Date: Feb. 8, 2001

(87) PCT Pub. No.: WO99/58046
PCT Pub. Date: Nov. 18, 1999

(30) Foreign Application Priority Data

| May 8, 1998 | (AU) | PP3424 |
| Jan. 19, 1999 | (AU) | PP8225 |

(51) Int. Cl.$^7$ ............................................. A61B 5/04
(52) U.S. Cl. ................................. 600/544; 600/558
(58) Field of Search .................... 600/544, 545, 600/558; 351/205, 237, 243, 246

(56) References Cited

U.S. PATENT DOCUMENTS

| 4,493,539 A | 1/1985 | Cannon, Jr. |
| 4,697,598 A | * 10/1987 | Bernard et al. .............. 600/544 |
| 4,736,751 A | * 4/1988 | Gevins et al. ............... 600/545 |

FOREIGN PATENT DOCUMENTS

| DE | 4030001 | 3/1992 |
| JP | 10-052402 | 2/1998 |

OTHER PUBLICATIONS

Graham, S.L. et al. (Jun. 1999) "Objective Perimetry in Glaucoma: Recent advances using multifocal stimuli" *Surv. Ophtalmol* 43(Suppl. 1):S199–S209.

Levy, N.S. and Korhnak, L., (1978). "The Monocularly Elicited Visual Evoked Response in Chronic Glaucoma," *Ann Opthalmol* 10(5): 551–555.

Klistorner, A.I. et al., (1998). "Multifocal Topographic Visual Evoked Potential: Improving Objective Detection of Local Visual Field Defects," *Investigative Ophthalmol & Visual Science* 39: 937–950.

Baseler, H.A. et al., (1994) "The topography of visual evoked response properties across the visual field" *Electroencephalography and Clinical Neurophysiology* 90:65–81.

Hood, D.C. et al., (May 2000) "An interocular comparison of the multifocal VEP: a possible technique for detecting local damage to the optic nerve" *Investigative Opthalmology and Visual Science* 41(6); 1580–1587.

\* cited by examiner

*Primary Examiner*—George Manuel
(74) *Attorney, Agent, or Firm*—Morrison & Foerster LLP

(57) ABSTRACT

The multifocal pattern visual evoked potential (VEP) has been adapted to detect visual field loss as a form of objective perimetry, with specific application to glaucoma. Multifocal pattern stimuli are cortically scaled and presented using a standard system. In order to effectively record the visual field responses, a unique array of bipolar occipital straddle electrode positions are employed, overlying the occipital visual cortex. Multi-channel VEP recording is then performed using these electrode positions. The responses are combined from the channels to produce a representation of the visual up to 25° of eccentricity. Analysis of results to detect early field defects is enhanced by asymmetry analysis between fellow eyes, and by a scaling algorithm to compensate for inter-individual variations. VEP objective perimetry corresponds well with subjective Humphrey visual field defects, showing loss of signal in the areas of visual field loss. Further, it shows reductions in areas of the visual field in glaucoma suspects where subjective testing is still within normal limits. This technique represents the first practical application of the multifocal pattern VEP to objective detection of visual field defects in glaucoma, and may have the potential for detecting disease at an earlier stage than conventional testing.

21 Claims, 26 Drawing Sheets

ELECTRODE POSITIONS

ELECTRODE POSITIONS

MULTIFOCAL PATTERN VEP

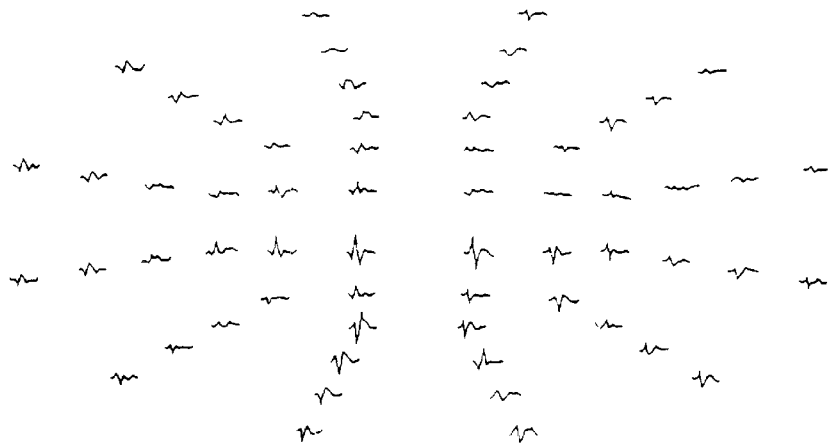
HORIZONTAL FIG. 8a
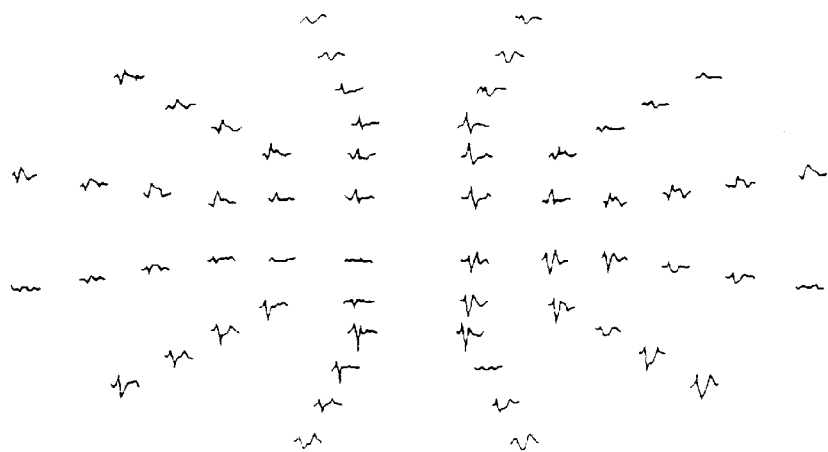
LEFT OBLIQUE FIG. 8b
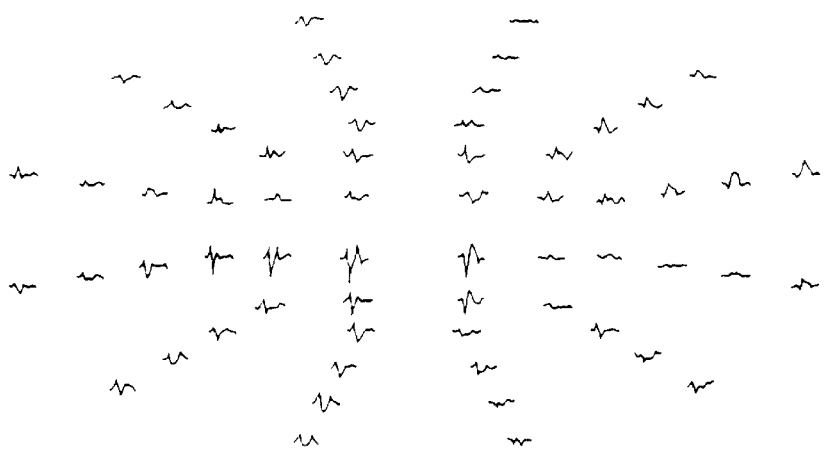
200nV  RIGHT OBLIQUE  FIG. 8c

HORIZONTAL CHANNEL

LEFT OBLIQUE CHANNEL

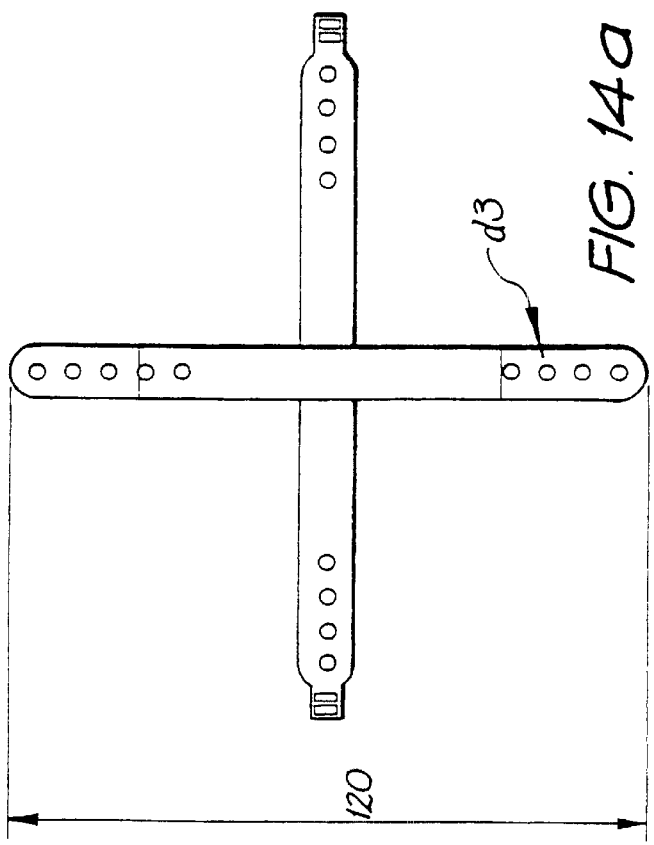
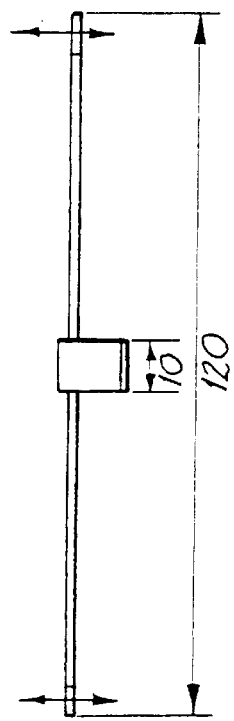

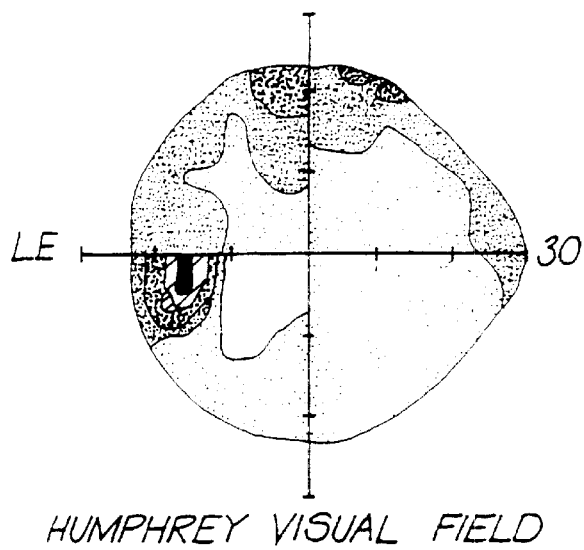
FIG. 15a HUMPHREY VISUAL FIELD
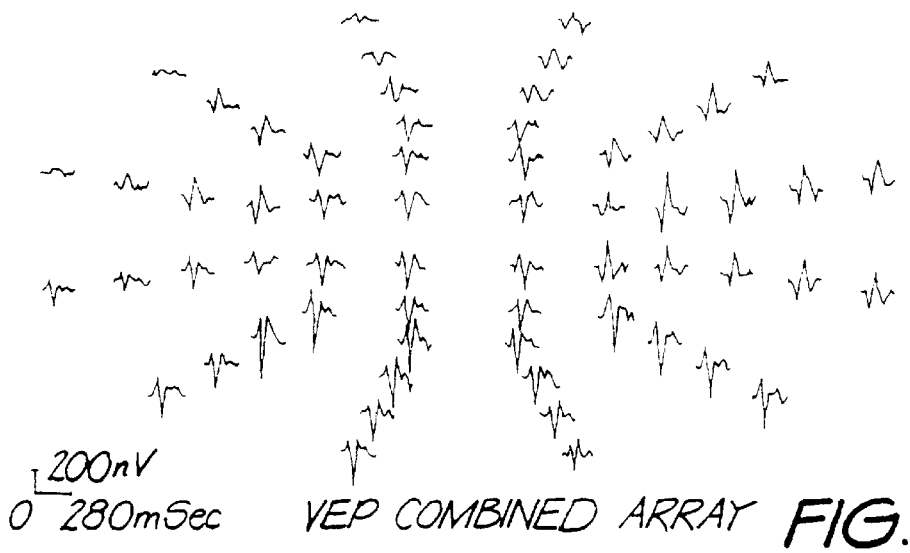
FIG. 15b VEP COMBINED ARRAY
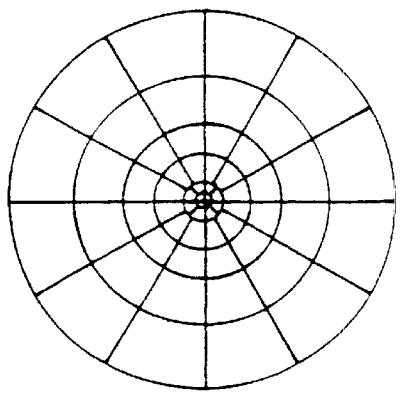
FIG. 15c ASYMMETRY COEFFICIENT (RAC)

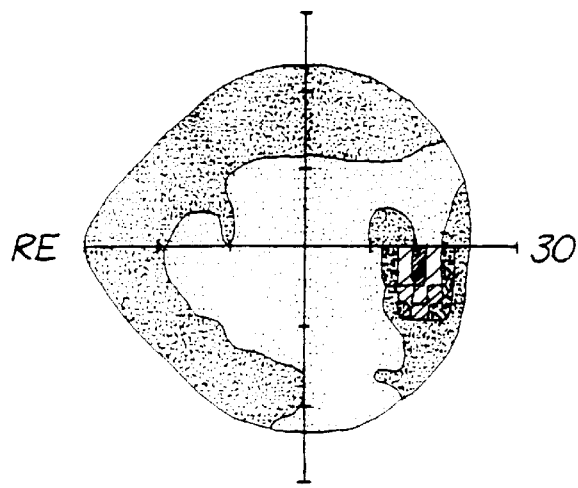
HUMPHREY VISUAL FIELD FIG. 15d
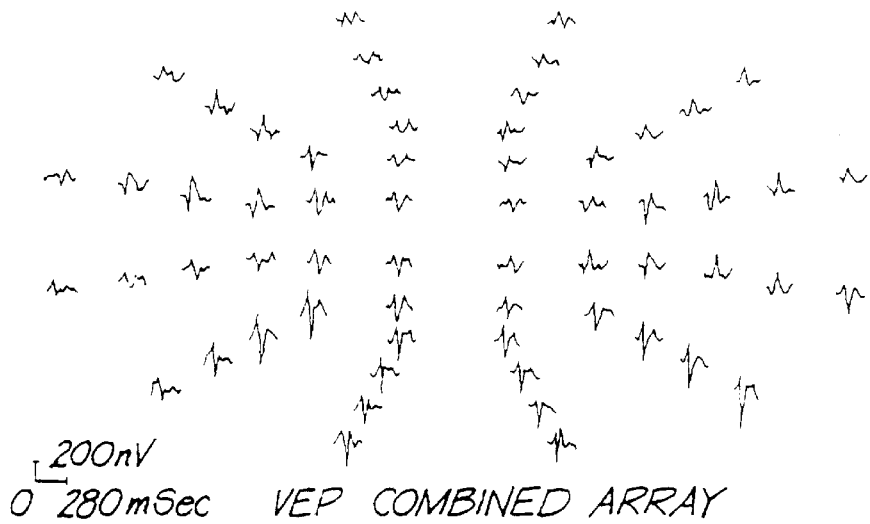
VEP COMBINED ARRAY
FIG. 15e
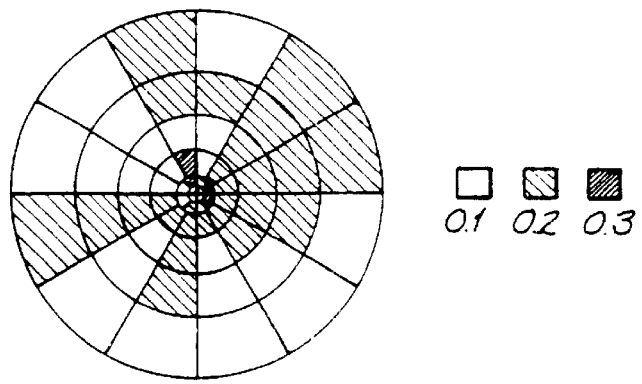
ASYMMETRY COEFFICIENT (RAC) FIG. 15f

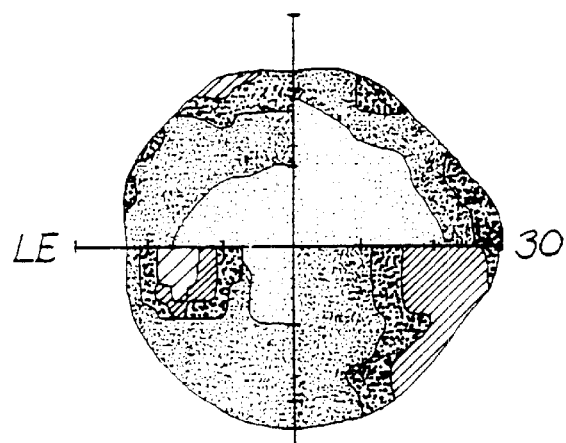
HUMPHREY VISUAL FIELD FIG. 16a
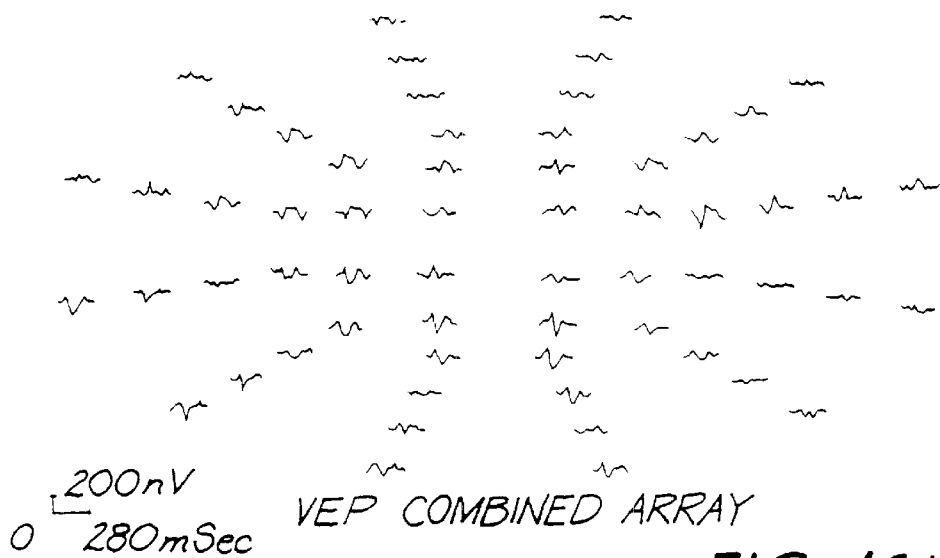
VEP COMBINED ARRAY FIG. 16b
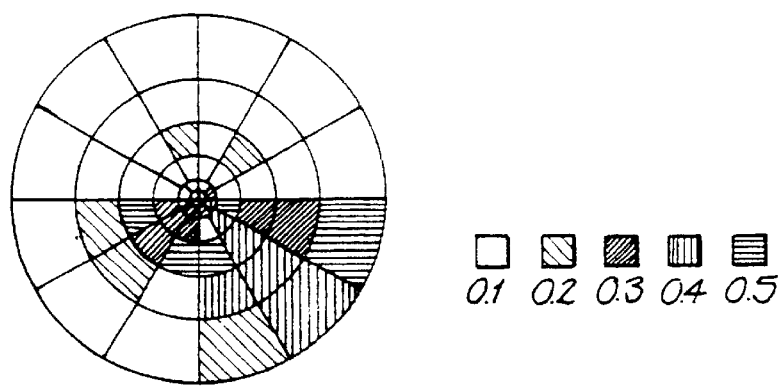
ASYMMETRY COEFFICIENT (RAC) FIG. 16c

HUMPHREY VISUAL FIELD

VEP COMBINED ARRAY

ASYMMETRY COEFFICIENT (RAC)

HUMPHREY VISUAL FIELD

VEP COMBINED ARRAY

ASYMMETRY COEFFICIENT (RAC)

HUMPHREY VISUAL FIELD

200nV
0 280mSec  VEP COMBINED ARRAY 0.1 0.2 0.3 0.4 0.5

ASYMMETRY COEFFICIENT (RAC)

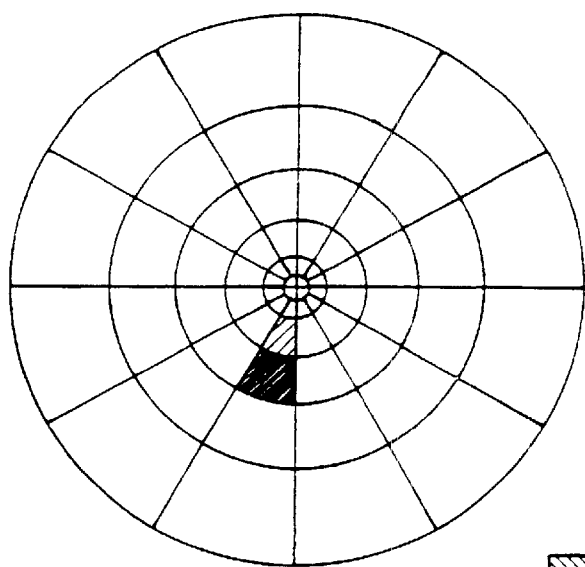
FIG. 18a
5%  1%  0.5%  0.1%
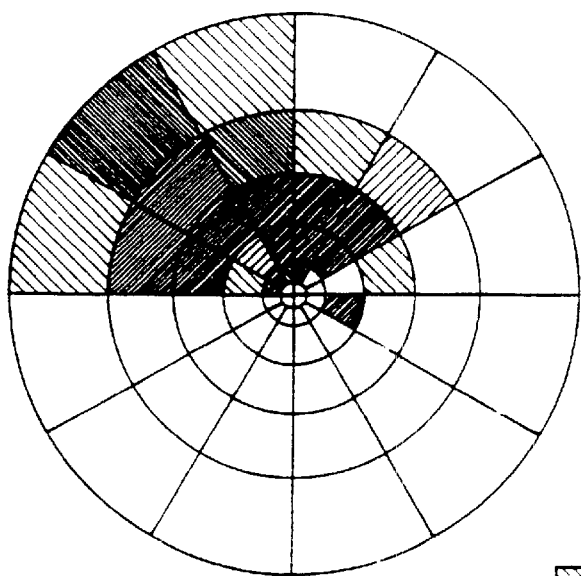
FIG. 18b
5%  1%  0.5%  0.1%

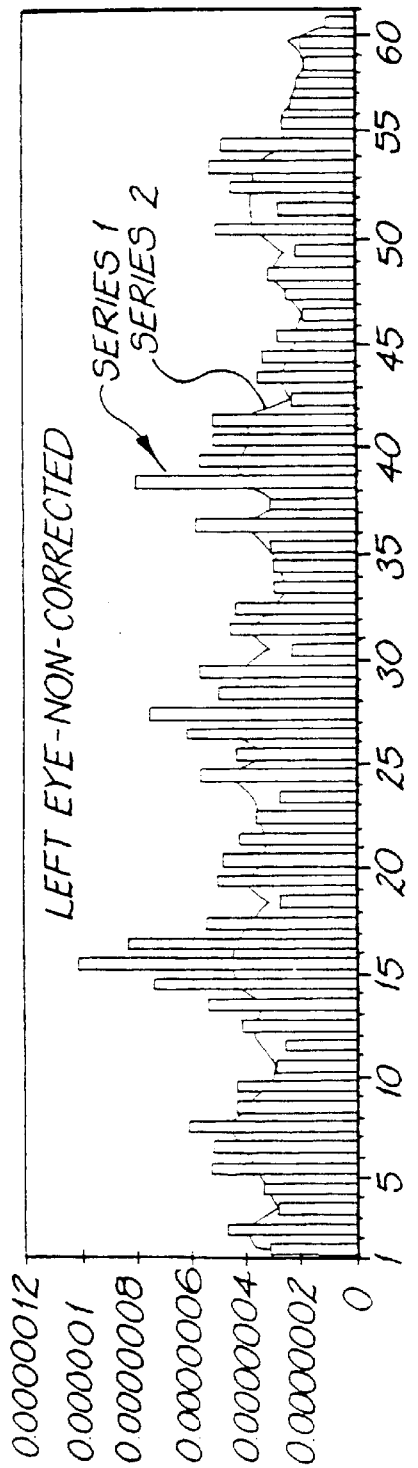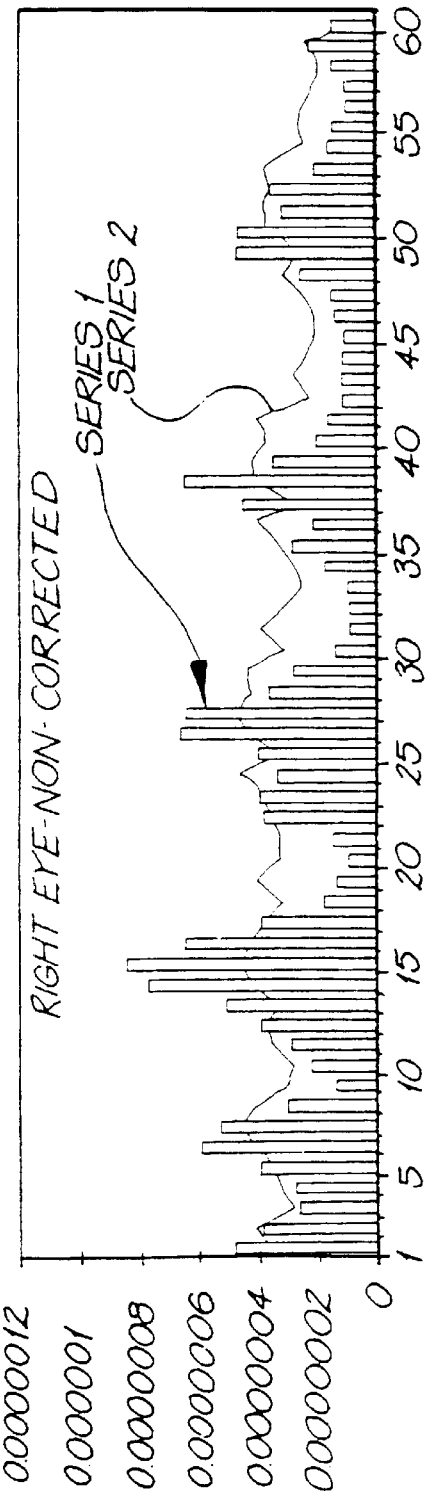

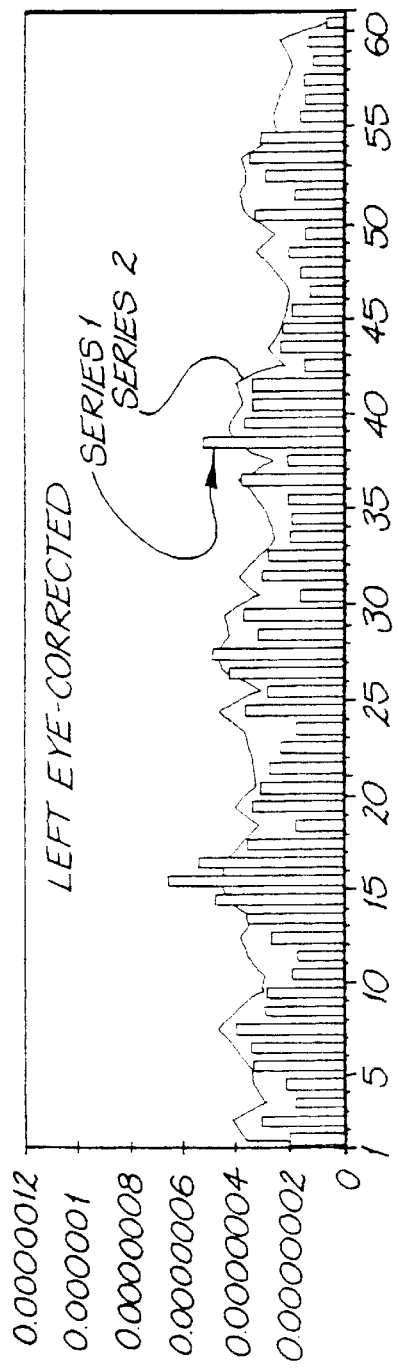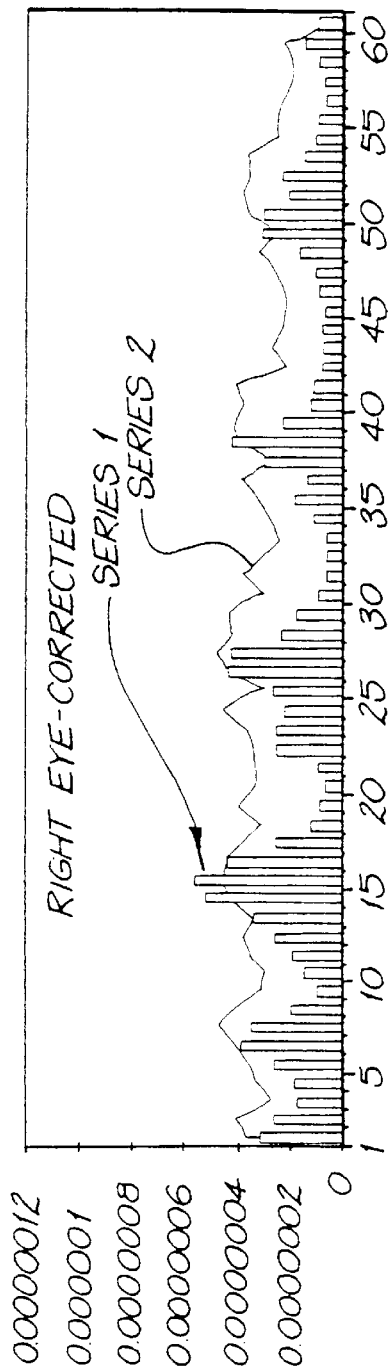

UNSCALED

SCALED

ELECTROPHYSIOLOGICAL VISUAL FIELD MEASUREMENT

TECHNICAL FIELD

This invention concerns an electrophysiological visual field measurement technique for the objective measurement of the visual field. The technique will be known as "Visual Evoked Potential Objective Perimetry" or "VEPO-Perimetry". There is a strong demand for such a measure to supplement the variable performances seen on automated perimetry and other psychophysical tests in the evaluation of glaucoma and other disorders of vision.

BACKGROUND ART

The conventional full field visual evoked potential (VEP) provides information mostly about the central visual field. It is reported to be abnormal in about half of the population with glaucoma—a disease which is one of the commonest causes of blindness. Since many patients can have normal responses, it does not have good discriminatory power for the detection of the disease. The variable findings have previously been explained by the fact that the VEP predominantly reflects macular function and in glaucoma the damage tends to affect central vision late in the disease.

There are several studies using stimulation of parts of the visual field to record VEPs. These have employed half-fields, quadrants, segments. annulus or peripheral field vs central field, and also local stimulation using light emitting diodes. These techniques greatly improve detection of the peripheral visual field defects, compared to full central stimulation. However, significantly higher responses from stimulation of upper hemiretina (lower visual field) compared with lower hemiretina (upper visual field) has often been reported.

A major advancement in stimulus and recording technology has recently been introduced which enables the presentation of a multifocal stimulus. This is now commercially available as the VERIS—Scientific™ system (Electro-Diagnostic Imaging, Inc., San Francisco) or Retiscan (Roland Instruments Wiesbaden, Germany) . These systems provide the opportunity for topographical analysis of recordings, with the capability of examining the effects of sequential flashes. This adds a time domain to the analysis and allows examination for temporal non-linearities in the response.

Visual stimuli are presented in a preset number of hexagons in arrays (or segments in a dart board) with the possibility of flash or pattern stimuli within each area. The stimulus areas can be cortically scaled which means that the area of each dart board segment increases with eccentricity, proportional to cortical magnification.

With VERIS or Retiscan it is possible to record a detailed multifocal ERG or VEP that show a topographic distribution of signal amplitudes. While results for ERG amplitudes are useful in delineating areas of outer retinal damage in some diseases (eg retinal dystrophies), they have not been shown to correspond with areas of glaucomatous nerve fibre loss and associated visual field defects. Using a multifocal VEP response recorded and analysed with the appropriate technique however, glaucoma field defects can be detected. The additional technique required for the appropriate extraction of the multifocal pattern VEP signal is the subject of this patent.

For VEP recording, the traditional and conventional electrode placement has been monopolar (occipito-frontal), with an active electrode (Oz) placed on the back of the head 2 cm above the inion, and a reference electrode (Fz) placed on the scalp at the front of the head; with a ground electrode placed on the earlobe.

SUMMARY OF THE INVENTION

The invention is a method of measuring the electrophysiological visual field. comprising the steps of:

placing a pair of electrodes around the inion on the scalp overlying the visual cortex of the brain, in addition to a ground electrode;

visually stimulating an eye; and, recording the data signals picked up by the electrodes. The technique is an objective method for assessing the visual field.

The data signals may be used to produce a VEP trace array.

The pair of electrodes are placed with the inion between them. They may be in line with the inion, or they may be placed in triangular relationship with the inion. The electrodes may be anywhere within a distance of 6 cm from the inion.

The electrodes may be placed at equal distances above and below the inion. and for instance may be 2 cm above and 2 cm below the inion. This placement may be termed bipolar occipital straddle or BOS placement.

An electrode may be placed at the position of the upper BOS electrode and another lower down on the midline below the position of the lower of the BOS electrodes, to measure a dipole between the upper of the BOS electrodes and the new electrode. The lower electrode may be 4 cm below the inion. This placement is called extended bipolar occipital.

An electrode may be placed on either side of the inion. The electrodes may be 4 cm on either side of the inion. This placement is called horizontal bipolar.

An electrode may be placed to the right of the inion and another below the inion. The electrode on the right hand side may be 4 cm to the right of the inion, and the lower electrode may be 4 cm below the inion. This placement is called right oblique.

An electrode may be placed to the left of the inion and another below the inion. The electrode on the left hand side may be 4 cm to the left of the inion, and the lower electrode may be 4 cm below the inion. This placement is called left oblique.

Previous attempts at field mapping have used electrode positions above the inion. Bipolar leads overlying the active occipital or striate cortex provide a superior assessment of the VEP from peripheral parts of the visual field. The projection of dipoles originating in the striate cortex subserving upper and lower hemi-fields onto the linking line between recording electrodes vertically straddling the inion is of similar magnitude but opposite polarity. This produces VEP signals from averaged upper and lower hemi-fields of similar amplitude but reverse polarity. As a result this placement produces approximately equal responses from the upper and lower hemifields.

The extended vertical BOS position with the lower electrode 4 cm below the inion improves the signal response compared to the standard BOS position (2 cm above and below). The horizontal bipolar electrodes provide a much greater signal from the test points along the horizontal meridian of the visual field. Improved detection in this area is extremely important for the application of objective perimetry to the detection of glaucoma. The oblique electrodes can also enhance the signal along the vertical midline of the visual field of the opposite side.

An electrode holder in the form of a convex cross, with a fixation strap across the forehead, is suggested to cover the electrode positions described above. It has the advantages of improving electrode contact, standardising electrode placement between tests and reducing muscle noise and artefacts.

The method may use unique electrode placement with a combined multiple channel VEP response. The post-recording analysis may involve an asymmetry analysis between eyes of the same subject, and an original scaling algorithm to reduce inter-subject variability. The method may utilise existing multifocal stimulation techniques.

Combination of Responses from Multiple Channels

One or more additional bipolar electrodes may be placed to record other channels of data input. A VEP may be recorded with more than one pair of bipolar electrodes to produce a multi-channel recording. Such a recording may then be combined in a single trace array to represent the visual field.

Ideally at least four channels are required to cover all possible dipole orientations. The greatest amplitude derived from all recorded channels at each individual point of the visual field is determined. It is then assigned to that point as the optimal signal. and its amplitude used as a measure of response of the visual pathway. The amplitude of signals within the combined array are subsequently used for data analysis.

Any multifocal stimulator (either existing equipment such as VERIS or Retiscan, or future systems) can be used to generate a cortically-scaled stimulus and extract a response. Raw data signals can be amplified by any biological amplifier by at least 100,000 times.

Multi-channel recording of the multifocal VEP using these electrode positions provides a considerable advantage in objective visual field mapping. By sampling from different bipolar electrode positions variously oriented around the striate cortex, an optimal response can be determined from each point within the field.

Asymmetry Analysis Between Eyes of an Individual Subject

The VEP trace from a particular sector of the combined trace array of one eye is compared to the amplitude of VEP from the corresponding area of the fellow eye and an amplitude ratio is calculated. The ratio is then compared to the normal ratio from the corresponding segment of the visual field from a normal data base and a probability of abnormality is calculated. This minimises the effects of within-eye asymmetry on interpretation of the response, and may help to reveal early pathological changes.

Scaling

To minimise the effects of inter-subject variability of amplitude, a scaling algorithm is employed to normalise data. This is based on the calculation of the largest responses within the field compared to normal values for that particular point. For instance using the tenth largest ratio of amplitude from both eyes to the normal mean value for the same point. The amplitudes of all points are then scaled up or down according to the ratio determined. This technique more effectively isolates visual field defects.

The combination of these recording and analysis techniques provides a form of objective perimetry, termed VEPO-Perimetry, which has potential advantages for clinical application particularly for the diagnosis and monitoring of glaucoma.

BRIEF DESCRIPTION OF THE DRAWINGS

Examples of the invention will now be described with reference to the accompanying drawings, in which:

FIGS. 8a, b and c show three VEP trace arrays recorded respectively from the horizontally placed electrodes and the two oblique channels. Simultaneous recording from the same subject as in FIG. 7. The trace arrays show substantial responses from the segments below the horizontal meridian. There was also a definite improvement in responses from some peripheral upper field locations, particularly in the oblique channels, when compared to the vertical channels alone.

FIG. 14a is a plan and FIGS. 14b and c are elevations of an occipital cross electrode holder with positioning holes for electrode clips—4 clips positioned with one on each arm. Standard distances from the inion are marked.

FIG. 15 is a between-eye asymmetry analysis of a glaucoma suspect showing early visual field changes. FIGS. 15a, b and c are respectively the Humphrey grey scale, the VEP trace array and a greyscale plot for the array for the left eye. FIGS. 15d, e and f are respectively the Humphrey grey scale, the VEP trace array and a greyscale plot for the array for the right eye.

FIGS. 17a, b and c are respectively the Humphrey grey scale, the VEP trace array and a greyscale plot for the array for the left eye.

FIGS. 18a and b show the respective probability values for the left and right eyes using the same analysis.

FIG. 19 demonstrates an example of non-scaled and scaled amplitude values for every segment of the stimulated visual field compared with a normal data base. Abnormalities are more readily seen on the scaled data.

DETAILED DESCRIPTION OF EXAMPLES OF THE INVENTION

Figure 1:
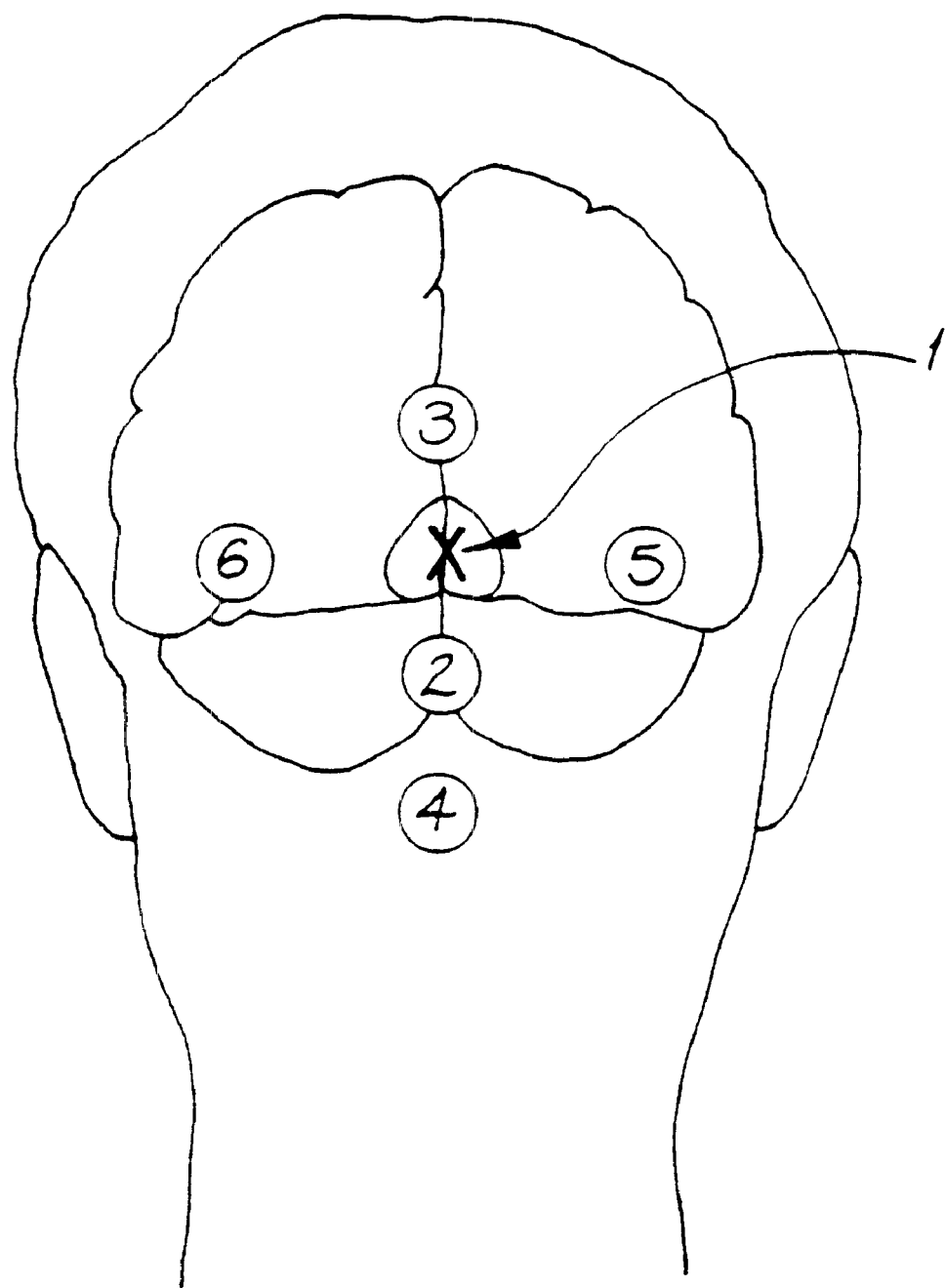
FIG. 1 is a rear view of a head showing electrode placement sites used in examples of the invention.

FIG. 1 shows the bipolar electrode placement positions on the back of the head. The inion 1 is the reference point for placement of the electrodes since this overlies the active occipital or striate cortex which is the visual centre of the brain. This fact is critical to success. since the electrode array is oriented around this area unlike previous VEP recordings which have used electrode positions either above the inion or in more remote locations.

A first pair 2 and 3 of the electrodes are placed at equal distances above and below the inion, and are 2 cm above and 2 cm below the inion. The negative electrode 2 is placed inferior and the positive electrode 3 superior to the inion. This placement is termed bipolar occipital straddle or BOS placement.

Figure 2:
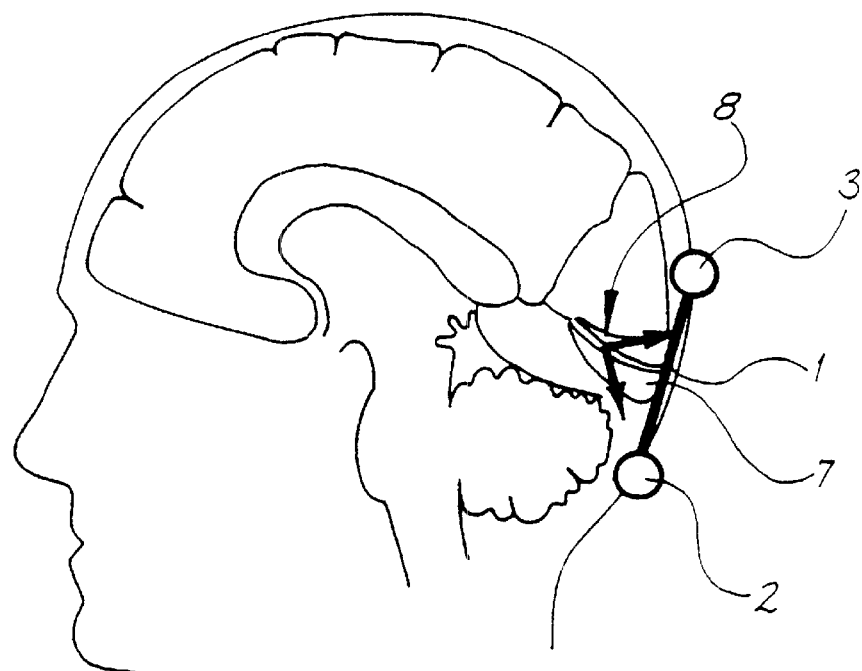
FIG. 2 is a side view of a head showing two electrode placement sites exemplifying the invention, and the generating dipole for the visual evoked potential (VEP).
Figure 3:
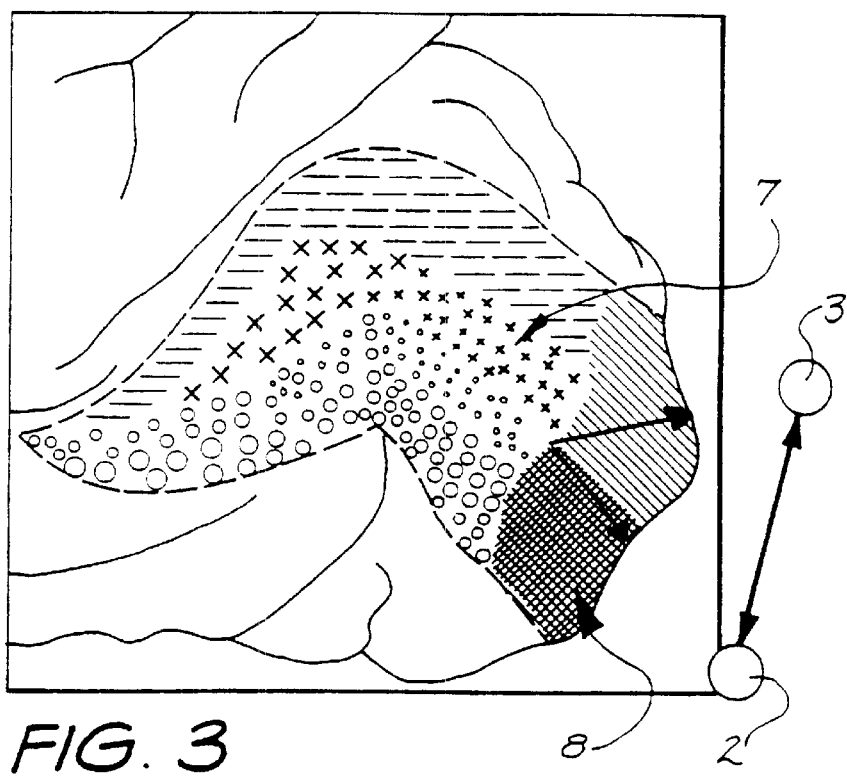
FIG. 3 is a detailed view of the generating dipole of FIG. 2.

FIG. 2 shows the bipolar occipital electrodes 2 and 3 from the side, and their position relative to the brain, and in particular the active occipital or striate cortex 7. The striate cortex can be seen to be divided horizontally by the calcarine sulcus into upper and lower hemifields. The BOS arrangement of electrodes is sympathetic to the cortical distribution of the visual field, with the upper hemifield representation being on the inferior surface of the occipital lobe, further away from the recording electrode on the occiput, and with its cells oriented differently from those of the lower visual field. The signals produced by the striate cortex are directed approximately as shown by the perpendicular arrows 8. and the electrodes can be seen to be positioned to receive these signals. FIG. 3 is a detail of the visual cortex of the brain from FIG. 2 , illustrating the direction of the dipoles.

One or more additional bipolar electrodes are placed to record other channels of data input.

Another electrode 4 is placed lower down on the midline below the position of the lower of the BOS electrodes 2, to measure a dipole between the upper of the BOS electrodes 3 and the new electrode 4. The lower electrode is 4 cm below the inion. This placement is called extended BOS.

Electrodes 5 and 6 are placed on either side of the inion. The electrodes are 4 cm on either side of the inion. This placement is called horizontal bipolar. It is important that the linking line between these electrodes is perpendicular to that of the vertical BOS channel, to cover all potential dipole orientations.

Single Channel Recording

Figure 4A:
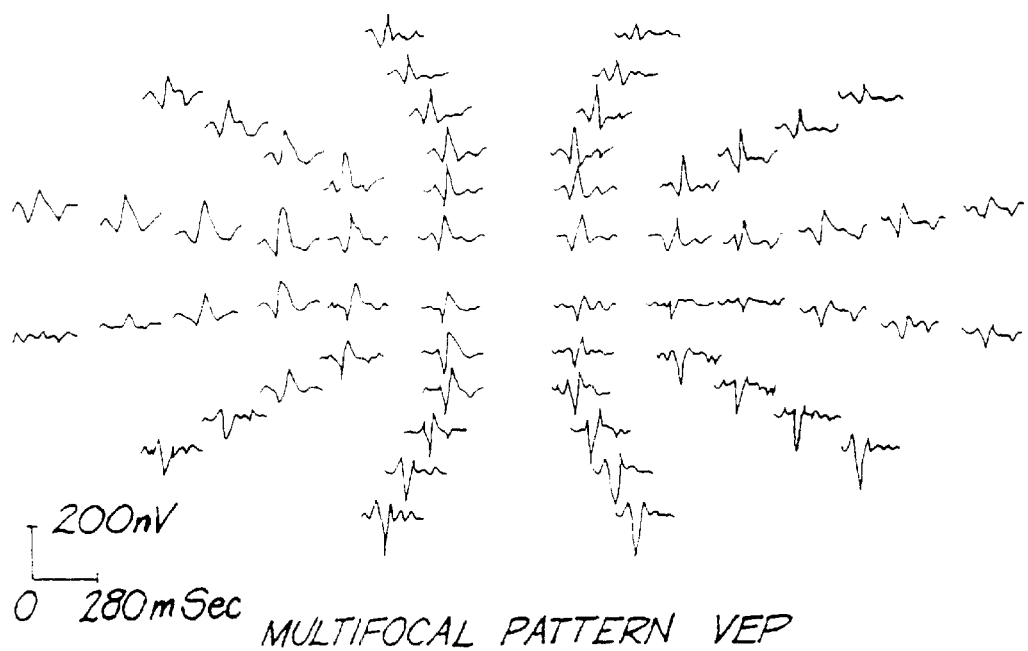
FIG. 4a is a single channel multifocal pattern VEP recording from a normal subject.

FIG. 4a is a multifocal pattern VEP recording taken from a normal subject. The figure shows a trace array of a first slice of the second order kernel. The tested area extends out to 25° of eccentricity. The bipolar electrode 2 and 3 allows the recording of a response of similar magnitude but opposite polarity from upper and lower visual hemifields. The signal amplitudes can be seen to be of similar magnitude throughout the field, which indicates normal vision.

Figure 4B:
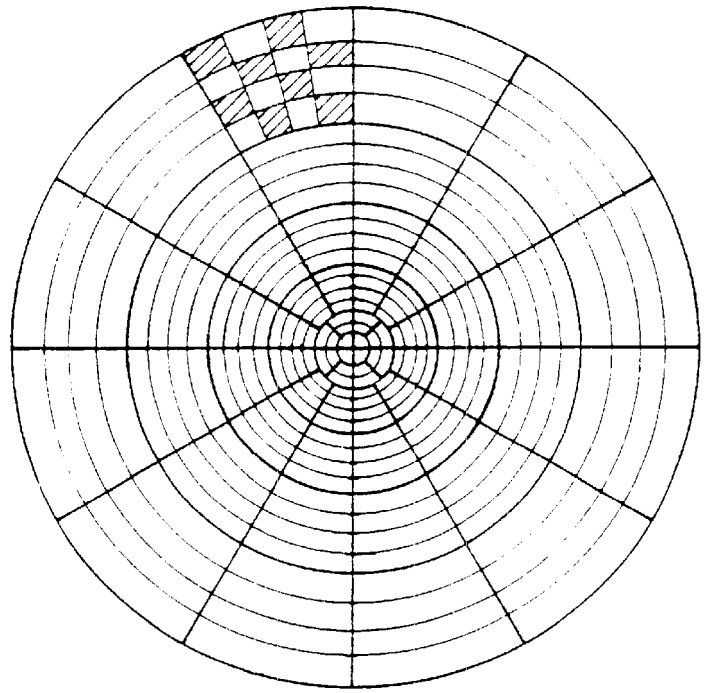
FIG. 4b shows stimulus dartboard configuration with pattern demonstrated in one of the 60 segments.
Figure 5A:
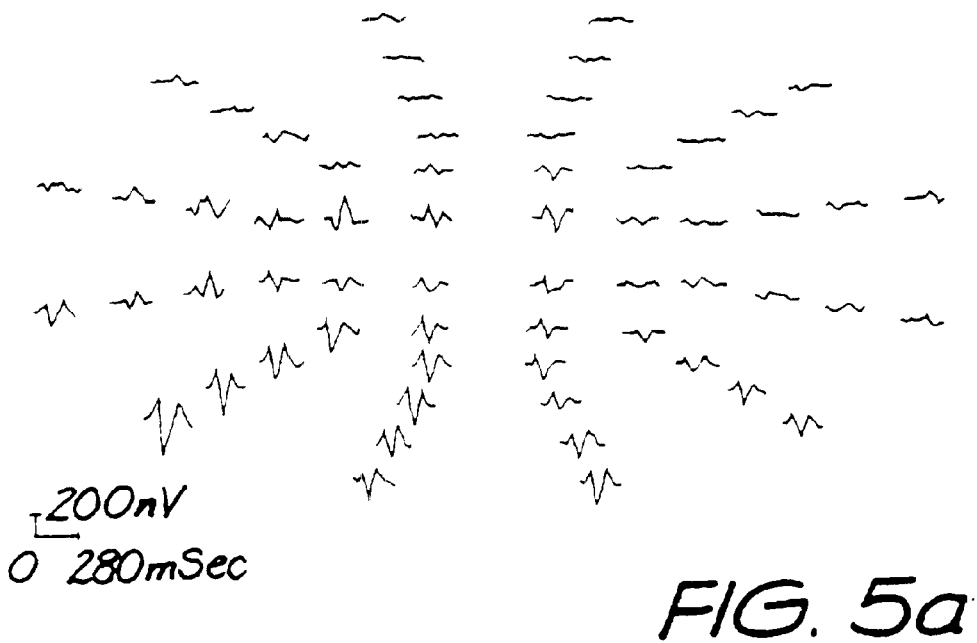
FIGS. 5 shows two examples of correlation between a single channel (BOS) multifocal pattern VEP trace array, FIGS. 5a and b, and respective Humphrey visual fields, FIGS. 5c and d.
Figure 5B:
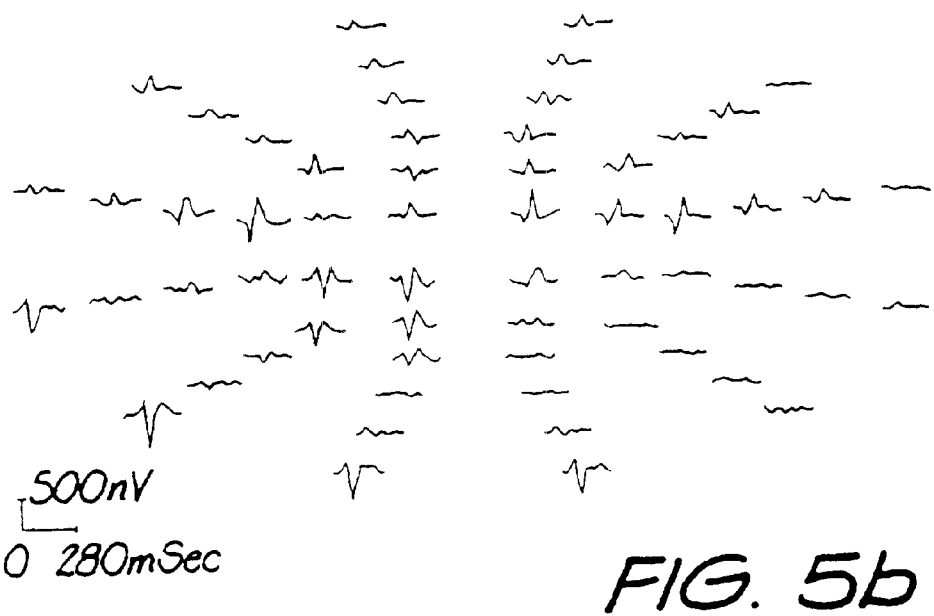
Figure 5C:
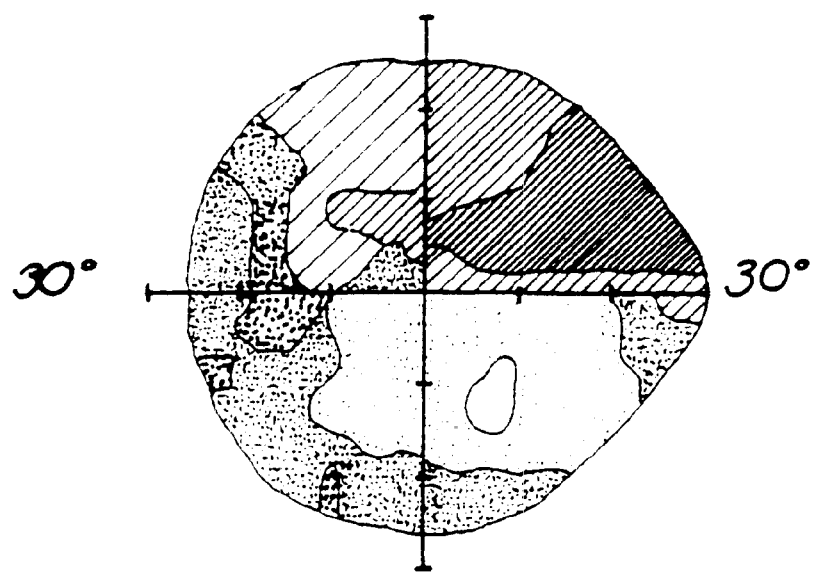
Figure 5D:
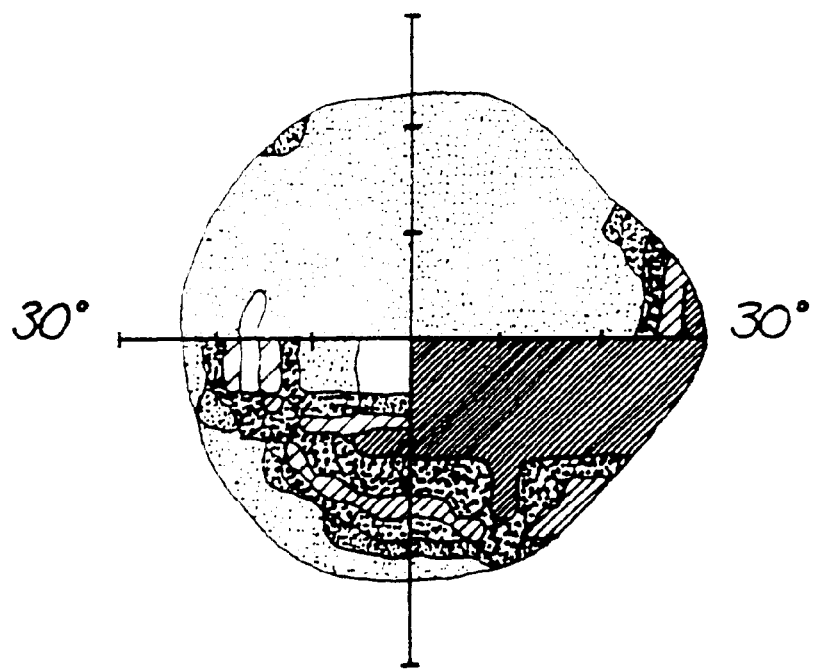

The visual stimulus is generated on a computer screen (stimulation rate 67 Hz) and is shown in FIG. 4b with a representation of the pattern in one of the sixty "dart board" segments. The segments are cortically scaled with eccentricity to stimulate approximately equal areas of cortical (striate) surface. The scaling is expected to produce a signal of similar order of amplitude from each stimulating segment. Each segment includes a checkerboard pattern of sixteen checks, with the size of individual checks being proportional to the size of the segment and therefore also dependent on eccentricity.

Subjects are comfortably seated in a chair and asked to fixate on a red fixation point at the centre of the stimulus pattern. The distance to the screen is 30 cm. corresponding to a total subtense of the stimulus of 50°. All subjects are optimally refracted. Pupils are not dilated. All recordings are collected using monocular stimulation. The signal is amplified 100,000 times and bandpass filtered between 3 and 100 Hz. The data sampling rate is 502 Hz. Raw data is scanned in real time and segments contaminated by a high level of noise, eye movements or blinking are rejected.

The first order kernel of the multifocal PVEP recordings (not shown) is flat, which confirms that the alternating pattern cancels out the luminance component. The first slice of the second order kernel contains a prominent and reproducible waveform and represents the interaction between the responses to two consecutive frames of the monitor. It is considered to be analogous to the conventional PVEP.

The inventors have examined a group of glaucoma patients in order to compare topographic signals with corresponding subjective Humphrey perimetric thresholds, using single channel BOS recording (Invest Ophthalmol Vis Sci,1998;39:937–950 and Surv Ophthalmol 1999, in press).

The study included 42 patients. Of these 36 had glaucoma and 6 were glaucoma suspects. Within the glaucoma group, 21 patients had primary open angle glaucoma (POAG) and 15had normal tension glaucoma (NTG). For the purpose of analysis, the Humphrey threshold quadrant totals were compared with the corresponding summed PVEP amplitude and the mean latency for the same quadrant.

The PVEP trace arrays recorded showed a good correlation with visual field defects seen in glaucoma patients. Two case examples are shown in FIG. 5. The field loss is reflected in the PVEP trace array. The corresponding area of the PVEP shows flat signals in the distribution of the field defect.

In all the 36 cases with a confirmed scotoma, an assessment of the trace array identified areas where the PVEP signal approached zero(<100 nV), and these corresponded to the scotoma area. In some cases with arcuate defects, the inventors have analysed the signal derived from Bjerrum-like superior and inferior arcuate regions, which mirrors the defect more accurately.

Figure 6:
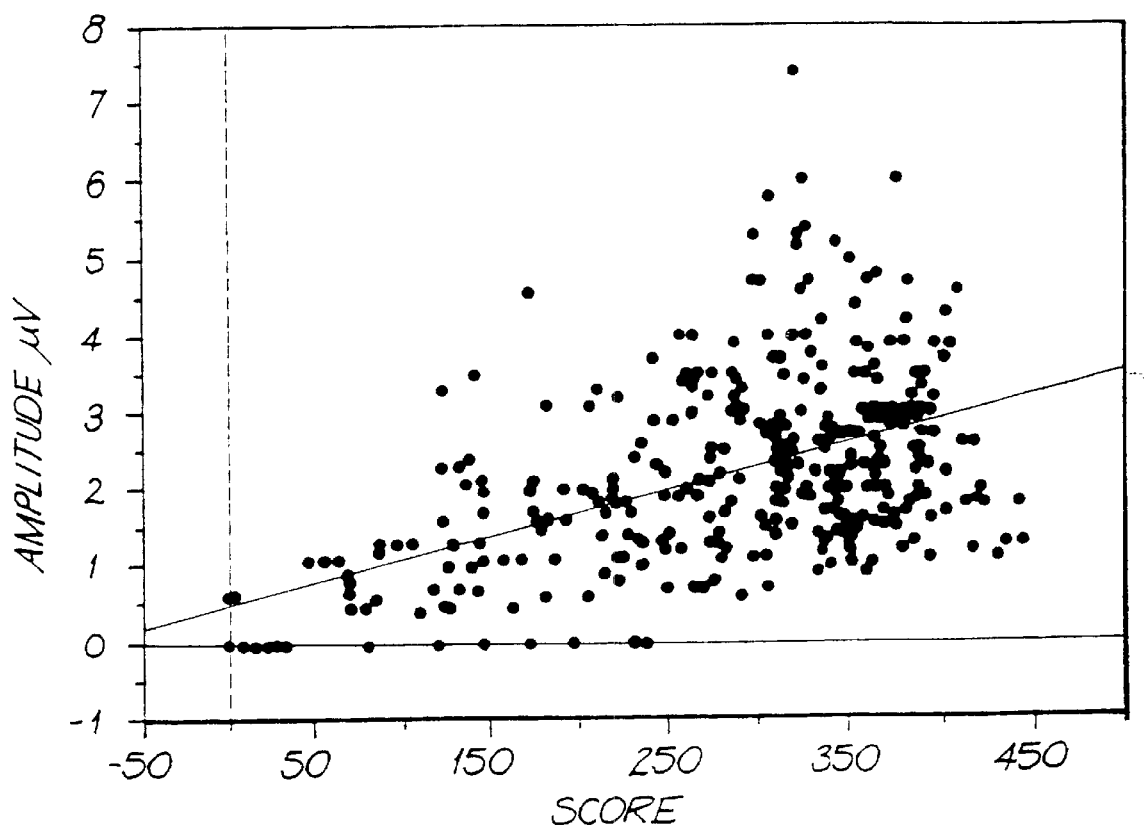
FIG. 6 is a graph illustrating the correlations between Humphrey threshold quadrant total dB scores and amplitude of pattern VEP for the same quadrant.

FIG. 6 shows the correlations between all Humphrey threshold quadrant total dB scores and pattern VEP amplitude for the same quadrant. Amplitude correlation is strong r=0.49, p<0.0001. Latencies showed weaker correlation at r=0.18 and r=−0.3 respectively.

One factor limiting this analysis is that there are differences in waveform characteristics in different parts of the field. On inspection of the trace array it can be seen that in some cases particularly in the upper hemifield, the waveforms closer to the vertical midline have a different polarity, which may be partially cancelling the signal when they are averaged. The inventors suggest a more accurate analysis of the PVEP traces would divide the array into sectors of similar waveform. Correlations with perimetric thresholds might then be even better.

There is a marked decrease in amplitude along the horizontal meridian seen in single channel BOS bipolar recordings. This may be due to one of two reasons: alteration of the dipole orientation or cancellation of upper and lower field components, or a combination of both. It is generally agreed that the horizontal meridian of the peripheral visual field is represented with slight individual variability deep within the calcarine banks at the fissure base. This may lead to such an alteration of dipole orientation that it may become much more perpendicular to the linking line between bipolar electrodes, minimising the recorded signal. The multi channel technique employing more than one electrode channel overcomes the problem of variable dipole orientation in the underlying cortex and extracts a reliable signal along the horizontal.

Multi-channel Recording

On the basis of cortical topography it was predicted that a horizontally oriented bipolar electrode straddling the inion would be optimal for registration of the horizontally oriented dipoles from the base of calcarine sulcus. This position was tested in 35 normal subjects, and 35 patients with field defects were also tested.

In an effort to increase the amplitude of all the recordable responses in the visual field, several other electrode positions were also tested. These included the extended (downwards) vertical BOS position, and the obliquely oriented electrodes (see FIGS. 1 and 2).

Figure 7A:
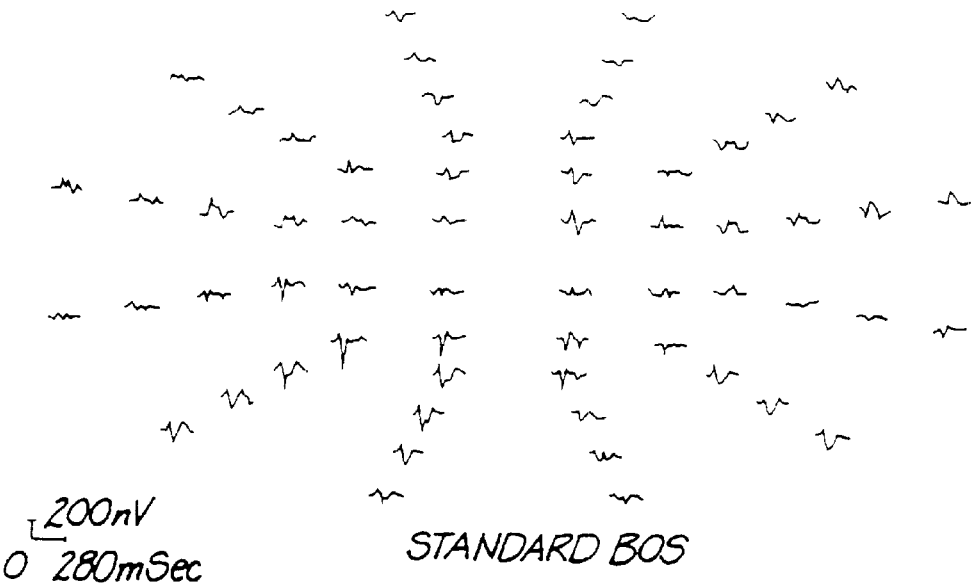
FIGS. 7a and b show two VEP trace arrays.

Testing confirmed that the extended BOS channel produced responses of practically identical waveform but significantly bigger amplitude than the standard BOS position; see for example FIGS. 7a and b, which respectively show trace arrays of standard and extended BOS recorded from the same subject in the same recording session.

Although the extended BOS electrode placement considerably increased the amplitude of the VEP as a whole, some of the individual stimulated areas of the visual field, particularly ones situated just below the horizontal meridian still produced very small responses. However, when horizontally placed (or in some cases oblique) channels were used the signal from those areas was significantly enhanced.

Figure 7B:
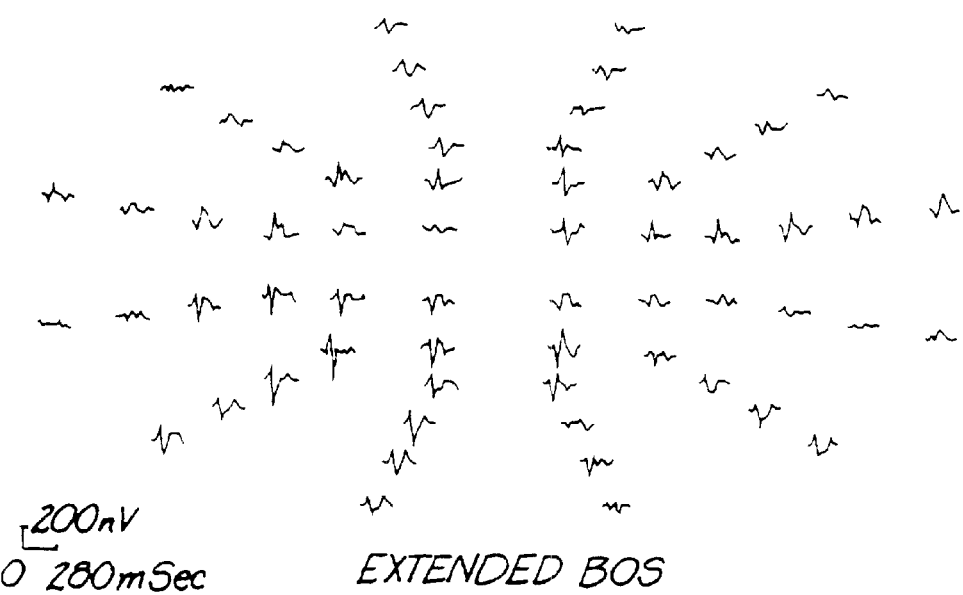
FIG. 7b shows the array from the vertical extended BOS channel, and it produces responses of practically identical waveform but significantly greater amplitude than the FIG. 7a array from the standard BOS position. The traces were recorded simultaneously from the same subject.

FIG. 8, presents traces recorded from horizontally placed electrodes, and the two oblique channels (the same subject and the same recording session as presented in FIG. 7). It shows substantial responses from the segments below the horizontal meridian. There was also a definite improvement in responses from some peripheral upper field locations, particularly in the oblique channels.

Figure 9:
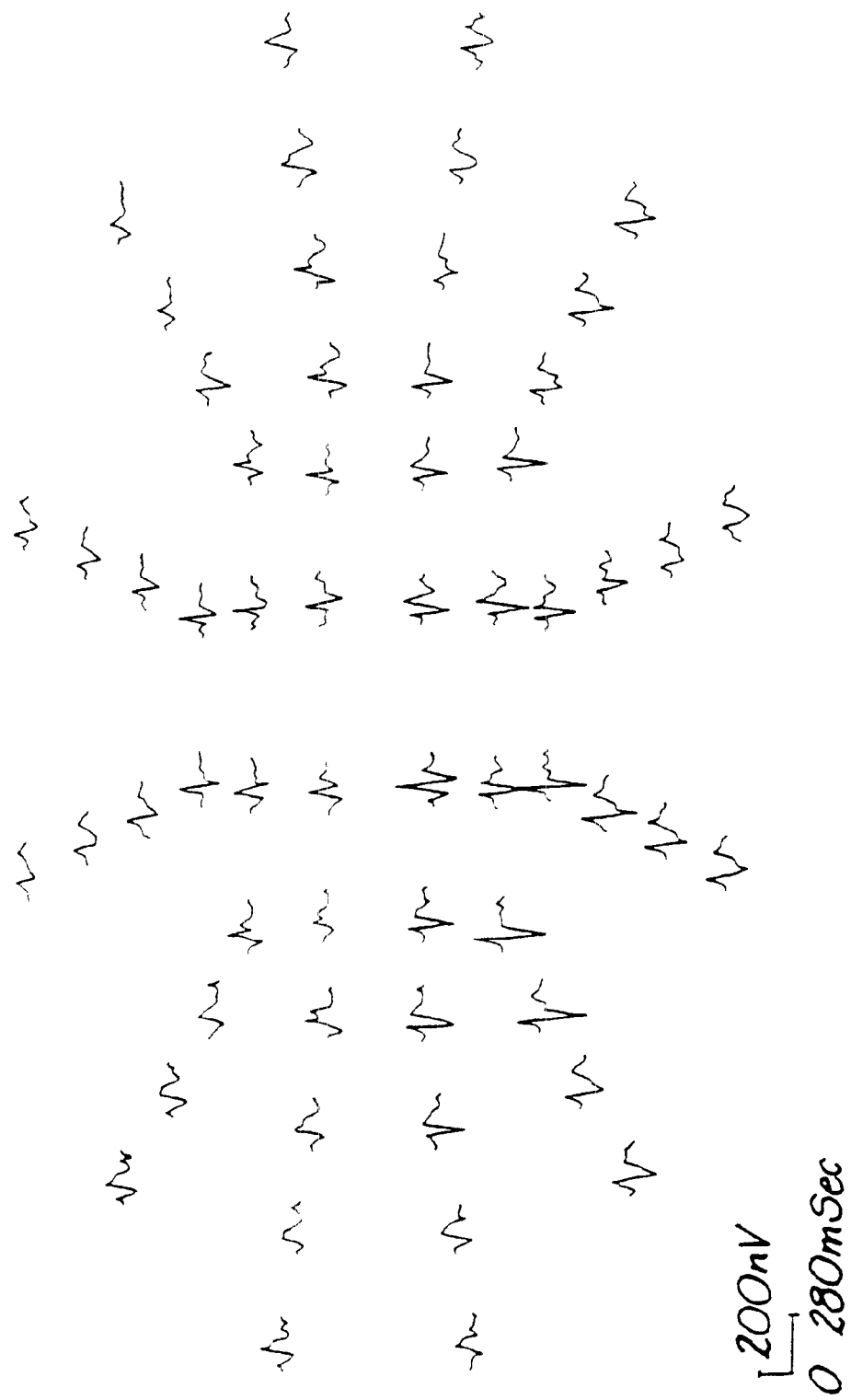
FIG. 9 is a combined VEP trace array derived from multi-channel electrodes presented in FIGS. 7 and 8 providing an overall representation of the visual field.
Figure 10A:
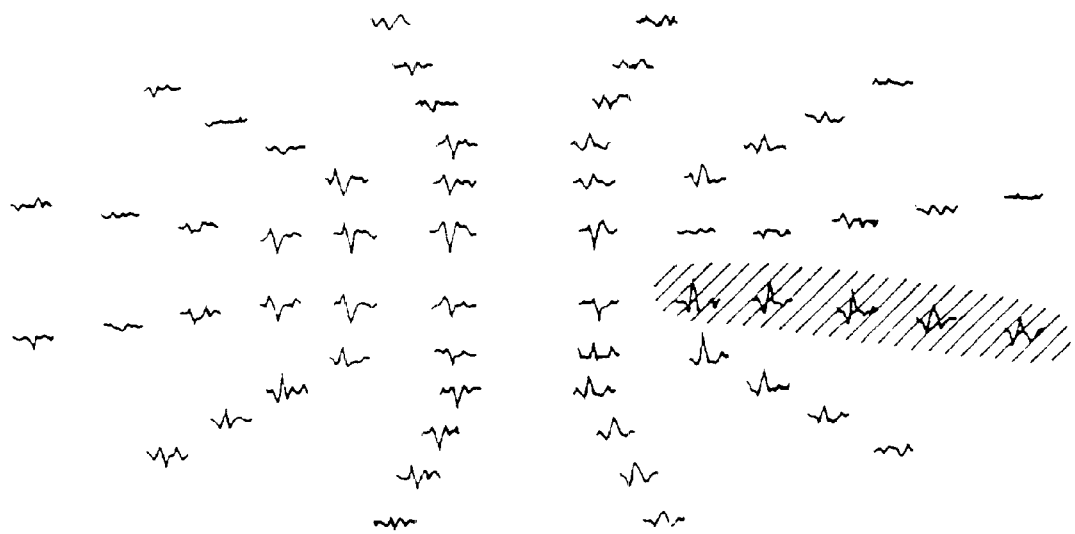
FIGS. 10a, b, c and d are a series of four trace arrays from a four channel VEP recording in a normal subject. The horizontal leads considerably increase VEP amplitude along horizontal meridian, see FIG. 10a. The oblique channels, FIGS. 10b and c, also help to improve derivation of the signals from peripheral part of the contralateral upper hemifield situated along the vertical meridian. These areas are circled.
Figure 10B:
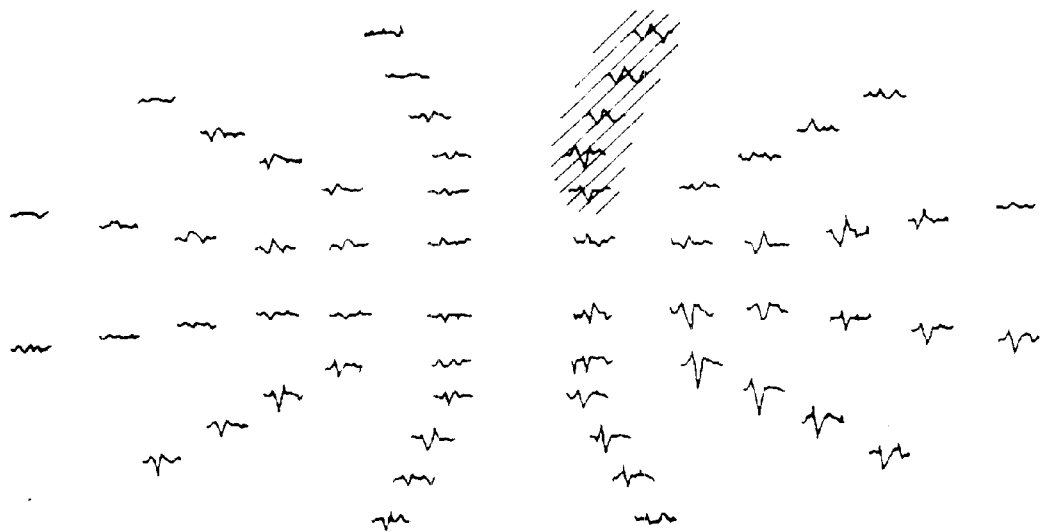
Figure 10C:
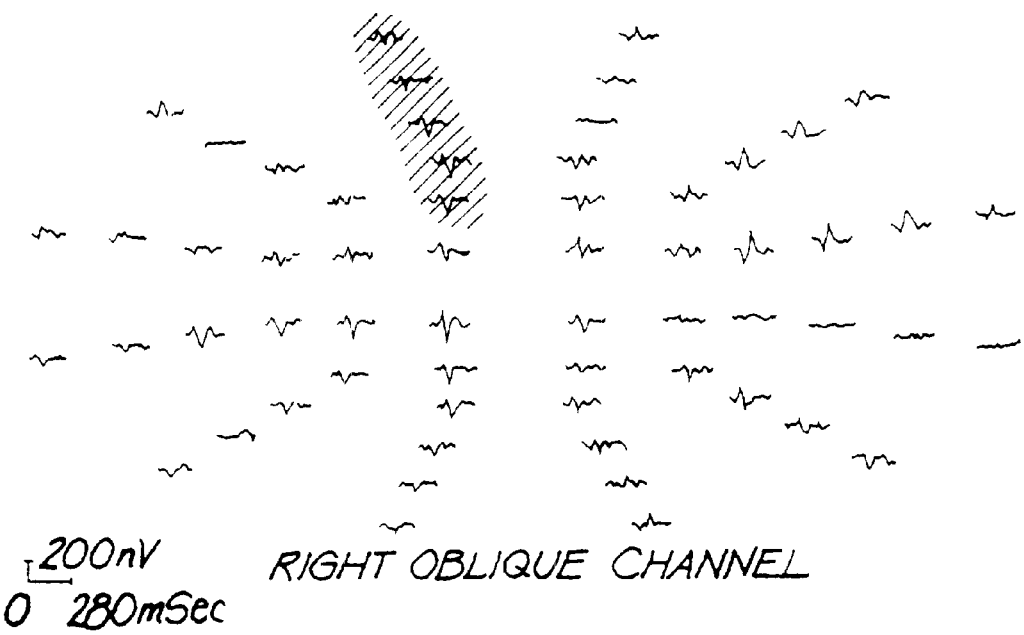
Figure 10D:
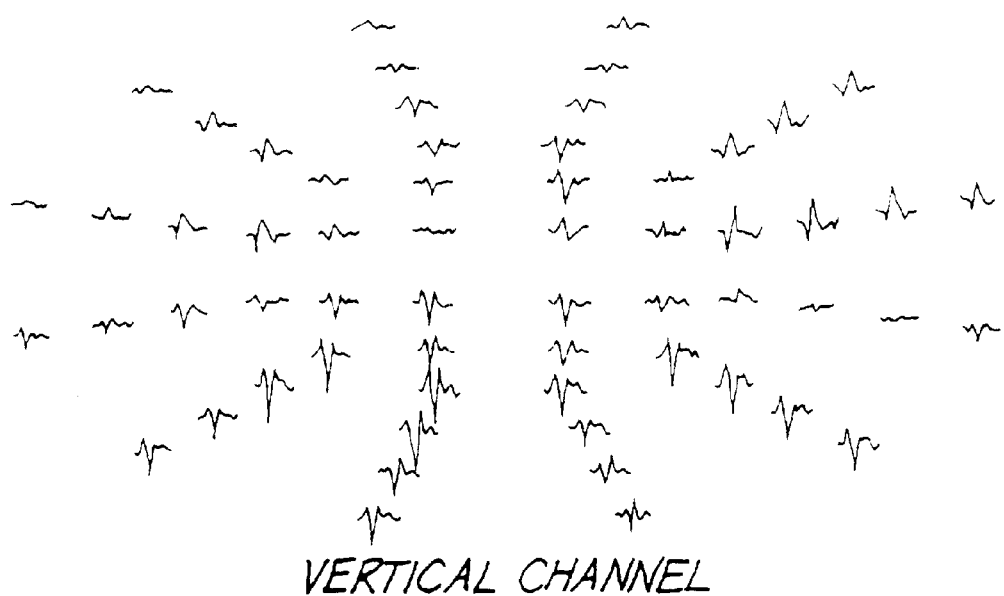

Peak-to-peak amplitudes for each wave within the interval of 50–150 msec were determined and compared between channels for every stimulated segment of the visual field. The wave of maximal amplitude from each segment was selected and a topographic map was created using customised software. An example of combined trace array is presented in FIG. 9 (the same subject as presented in FIGS. 7 and 8).

It is evident that the combination of the traces from different channels produced a much more uniform response throughout the whole tested visual field.

Figure 11:
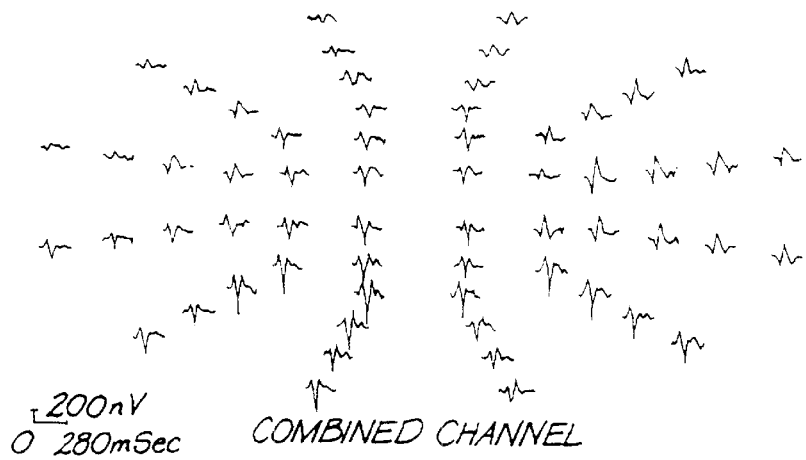
FIG. 11 is a multi-channel array combined from the four channels of FIG. 10. If only the vertical channel had been recorded, an impression of field loss in the form of a nasal step and superior defect would have been suggested. The combined array shows good responses throughout the field.

Another example of combination of the multi-channel recording is presented in FIGS. 10 and 11. Traces from all four channels are shown in FIG. 11. While the horizontal leads considerably increase VEP amplitude along horizontal meridian. the oblique channels also help to improve derivation of the signal from peripheral part of the contralateral upper hemifield situated along the vertical meridian.

Figure 12:
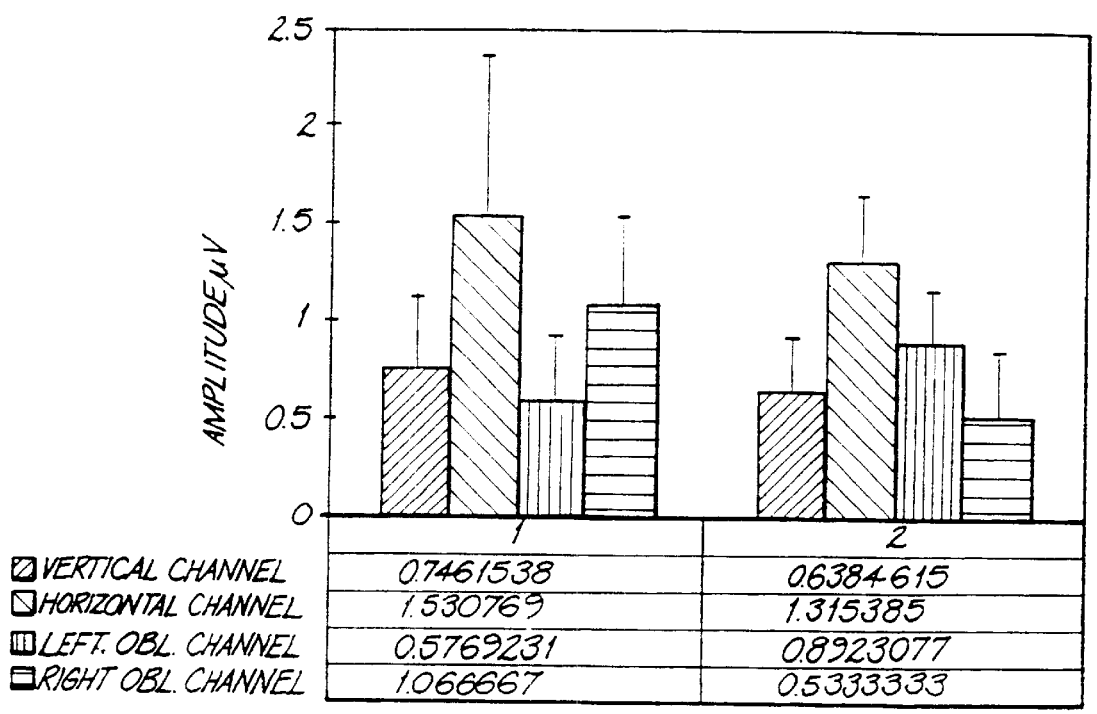
FIG. 12 is a histogram of responses from four channels along the inferior horizontal meridian. It demonstrates that horizontal electrode placement improves the amplitude of the responses from the segments below the horizontal meridian by more than 100%.
Figure 13A:
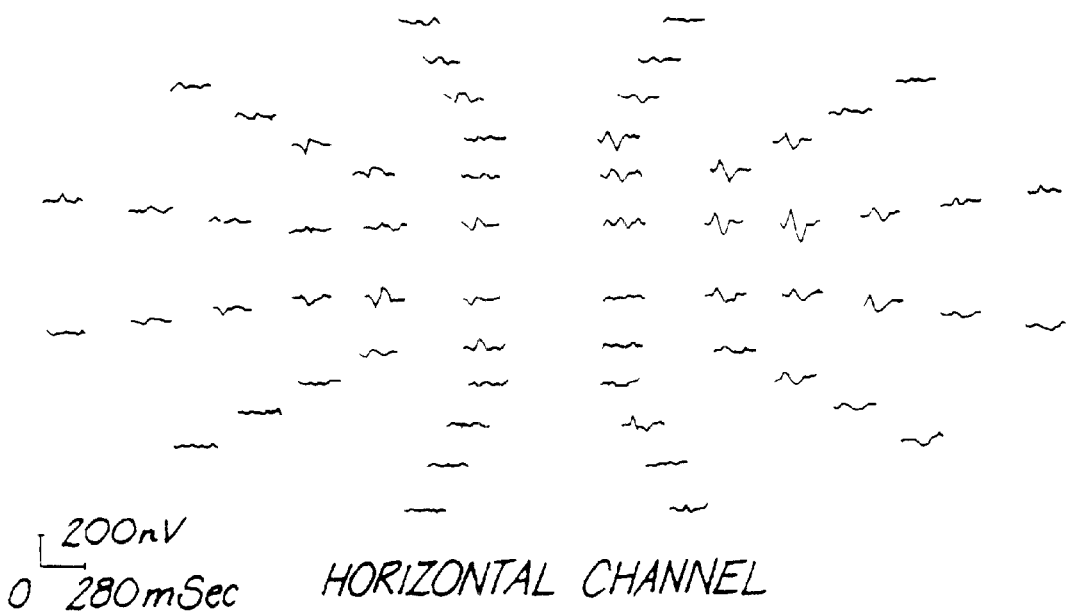
FIG. 13 is a comparison between four channel VEP, FIGS. 13a, b and c are the horizontal, vertical and combined channels, recorded from a patient with primary open angle glaucoma and the Humphrey field grey scale.
FIG. 13d. In each case the non-responsive parts of the field have been shaded. The scotoma area is seen to be less when the combined responses are taken into consideration, and to more accurately correspond to the visual field.
Figure 13B:
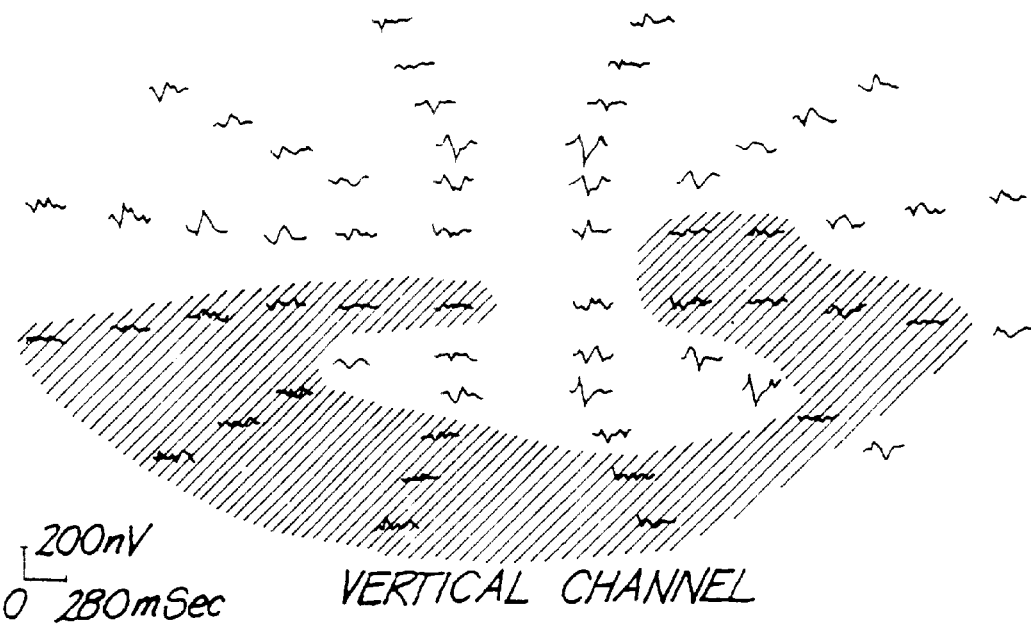
Figure 13C:
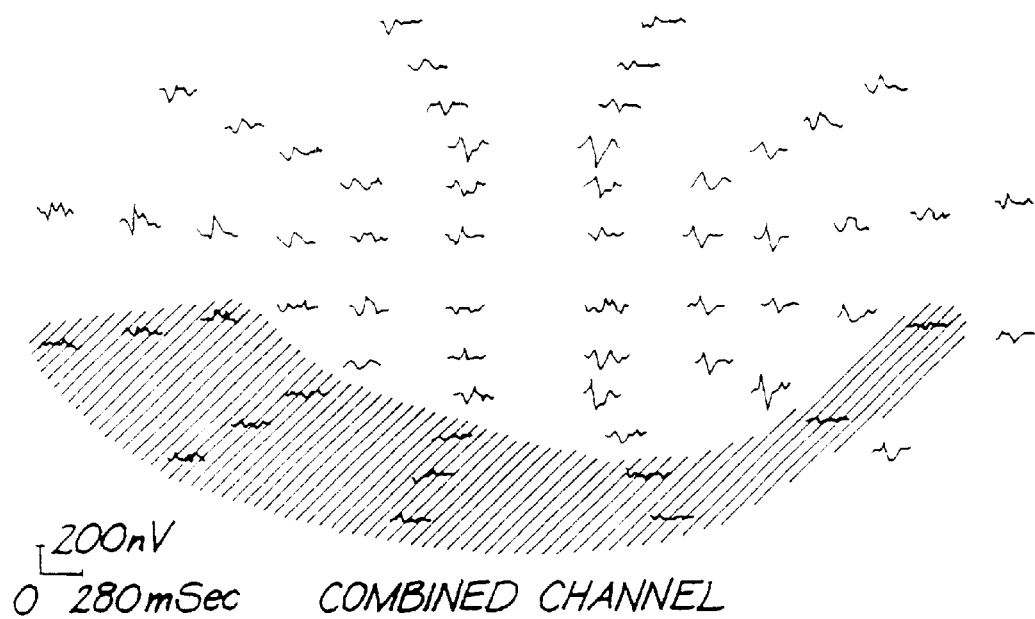
Figure 13D:
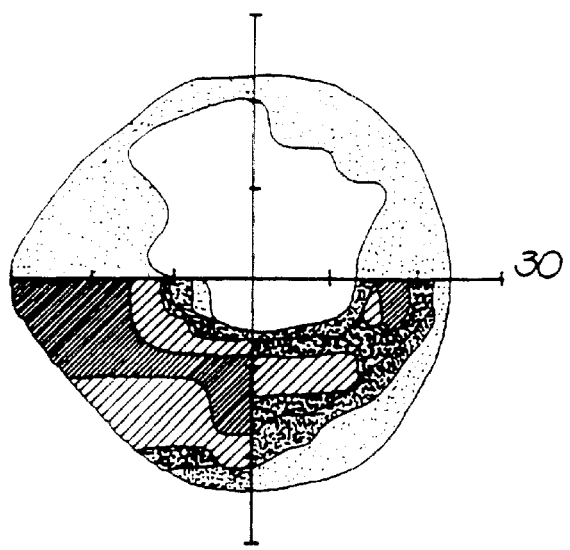

Quantitative assessment of the effectiveness of the multi-channel recording revealed that horizontal electrode placement improved the amplitude of the responses from the segments below horizontal meridian by more than 100%. FIG. 12 shows the relative amplitudes of the four channels for the six points just below the horizontal meridian. The temporal and nasal sides of the field are analysed separately. The difference between the vertical and horizontal responses was highly statistically significant (P=0.004 and P=0.00001 for temporal and nasal side of the visual field respectively).

To show the clinical importance of multi-channel recording in the objective assessment of the extent of visual field impairment, an example of multi-channel VEP recorded from a patient with glaucoma is presented in FIG. 13. Four channel recordings were performed and traces combined. Right and left oblique traces are not shown in the figure. The non-responsive parts of the field have been shaded in the vertical and combined channels only. The scotoma area is seen to be less when the combined responses are taken into consideration, and to more accurately correspond to the subjective visual field.

For optimal recording of the VEP response it is crucial to achieve good electrical contact, and to have the patient relaxed and comfortable. Using an electroencephalogram (EEG) cap with modified electrode positions, had the advantage of standardising electrode positions, but did not provide good appositional contact over the occipital region. If elasticised straps are employed to pull the cap downwards this has the effect of tightening the neck muscles, producing significant muscle noise. Also since the cap is made from fabric and is flexible there is still the possibility of some variation in electrode positioning between tests.

We have designed for multi-channel recording an occipital cross electrode holder that standardises the positions of the electrodes reliably in relation to the inion (see FIG. 14). It provides better apposition of the electrodes to the scalp, with the benefit of much less noise in the recording. As a result it is possible to reduce the recording time since less signal averaging is required to achieve a clean signal. It has adjustable electrode positions along each arm for different sized heads (one size fits all), and this also permits further experimentation with variations in electrode positioning. Since it does not cover the whole head it is cooler and more comfortable for the patient, and neck muscles remain relaxed.

The construct is of two curved flexible plastic arms in a cross shape. The horizontal arms are attached to a broad elasticised strap that encircles the forehead and keeps the four contact points of the cross, where the electrodes are located, firmly applied to the scalp. The arms have holes positioned and marked at 5 mm intervals along each, into which the electrode clips can be inserted, not only into our standard positions but to allow further modification of the electrode array.

Asymmetry Analysis

The multi-focal VEP in normal subjects shows significant amplitude and waveform variation of individual signals across the field. Detailed comparison of VEP trace arrays recorded from both eyes of normal subjects, however, revealed remarkable similarities in the waveform and amplitude of the individual signals from the corresponding segments of the two eyes of an individual. This suggested that the major part of the "within eye" asymmetry is due to the underlying cortical convolution.

In the early stages of disease the amplitude of the locally evoked cortical signal might only be reduced, not totally extinguished. The "within eye" asymmetry of the VEP signal could then limit the use of the multi-focal VEP in the recognition of a small amplitude reductions seen with early pathological change. Thus, to minimize the effects of within eye variation on the detection of early change, "Asymmetry Analysis" of the VEP is suggested. The amplitude of the VEP trace from a particular segment of the combined trace array of one eve is compared to the amplitude of the VEP from the corresponding area of the fellow eye and an amplitude ratio is calculated.

The ratio is termed the Response Asymmetry Coefficient (RAC). The RAC is then compared to the normal ratio of the corresponding segment of the visual field from a normal data base and a probability of abnormality for that point of the visual field is calculated.

The inventors have observed that in several of the high risk suspects who had abnormal optic discs but still normal Humphrey visual fields in both eyes, cases were seen of asymmetric VEPs where there were clear differences between the VEP responses of the two eyes in parts of the visual field that remained with normal thresholds. This may imply that PVEP changes precede the development of field defects, and that this form of objective perimetry may prove to be an earlier marker for glaucomatous damage than standard testing.

FIG. 15 demonstrates an asymmetry analysis of a glaucoma suspect. It shows that while the multifocal VEP responses of right eye are present practically at every location of the stimulated visual field, their amplitude is significantly reduced compared with left eye, thus indicating early changes.

A greyscale plot shows that the calculated RAC reaches 0.4 in some areas. The Humphrey visual fields are still normal in both eyes.

Figure 16D:
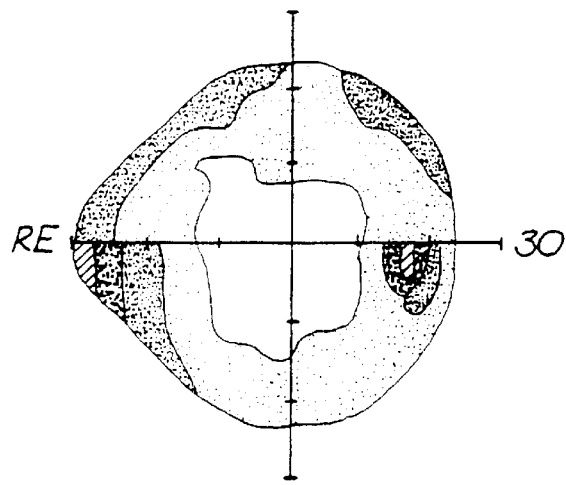
FIGS. 16d, e and f are respectively the Humphrey grey scale, the VEP trace array and a greyscale plot for the array for the right eye.
Figure 16E:
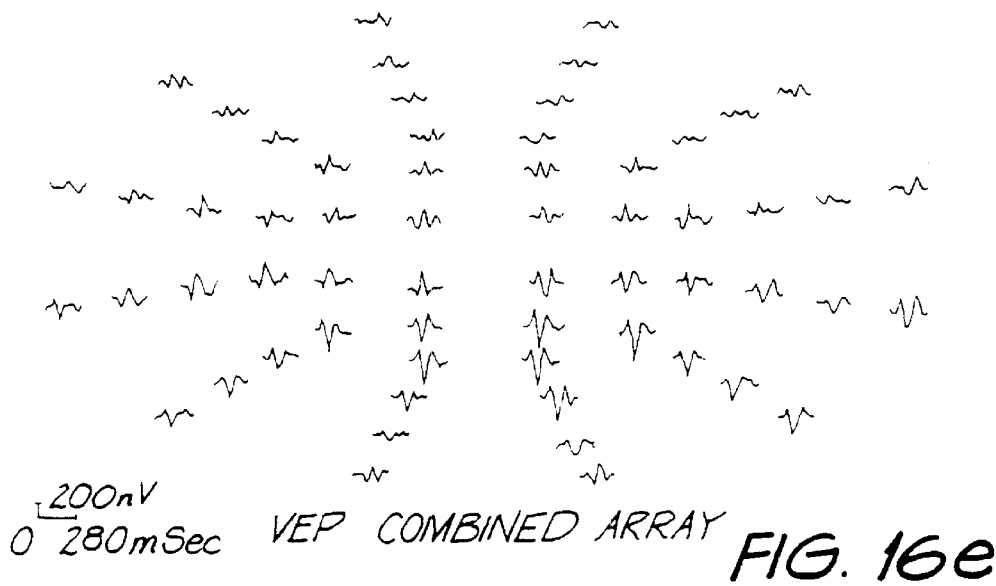
FIG. 16 is an asymmetry analysis of a patient with early glaucoma and an inferior arcuate defect.
FIGS. 16a, b and c are respectively the Humphrey grey scale, the VEP trace array and a greyscale plot for the array for the left eye.
Figure 16F:
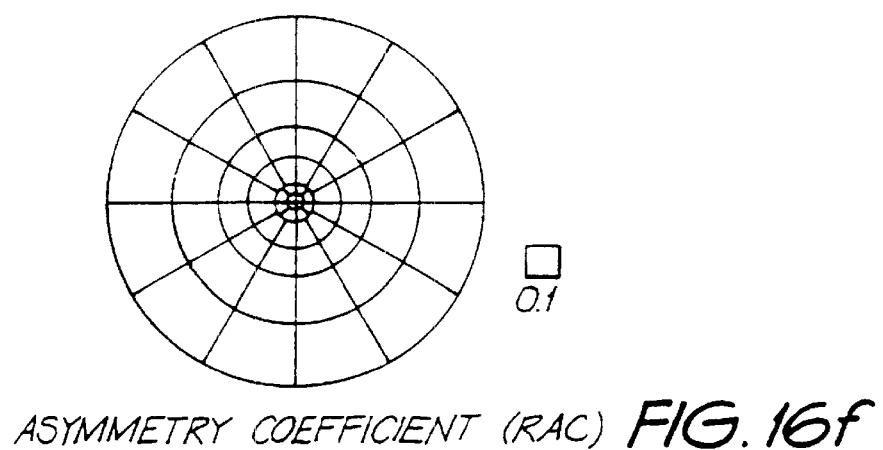
Figure 17A:
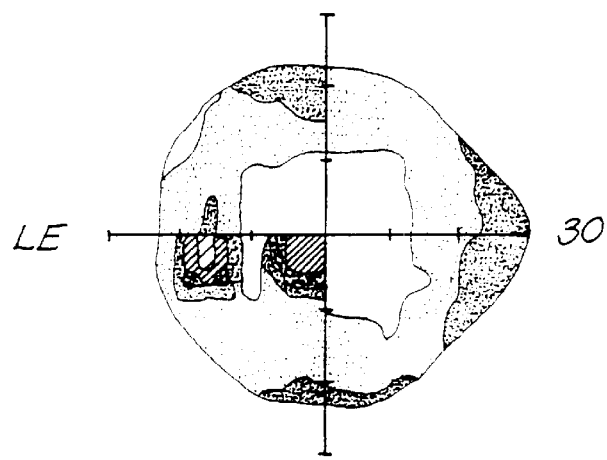
FIG. 17a is an asymmetry analysis of a patient with normal tension glaucoma and superior arcuate defect.
Figure 17B:
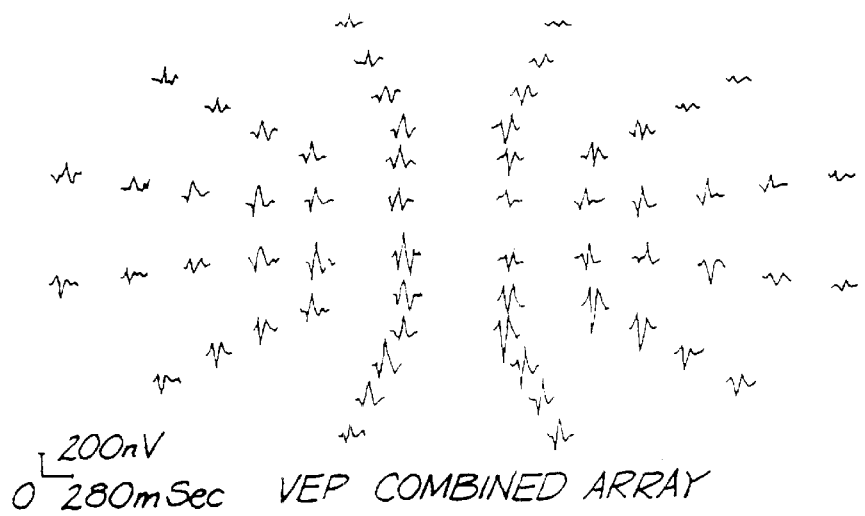
FIGS. 17d, e and f are respectively the Humphrey grey scale, the VEP trace array and a greyscale plot for the array for the right eye.
Figure 17C:
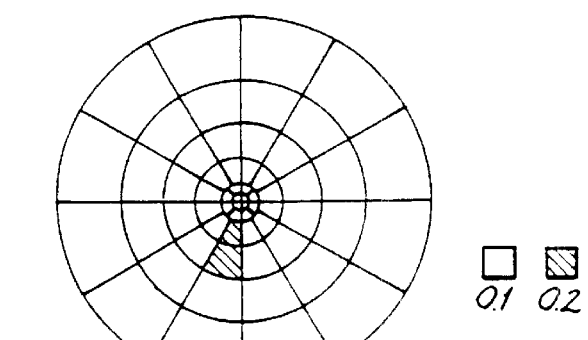
Figure 17D:
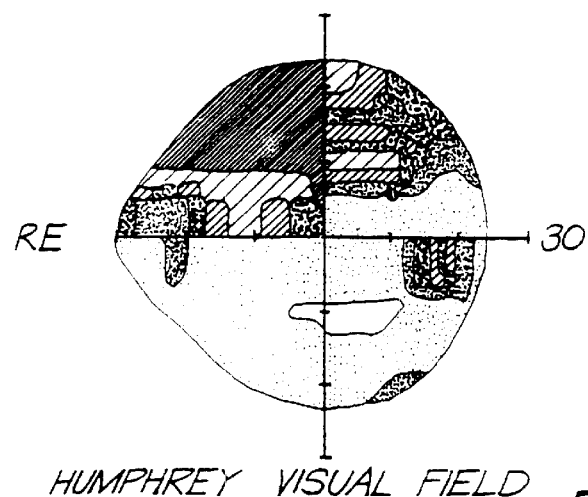
Figure 17E:
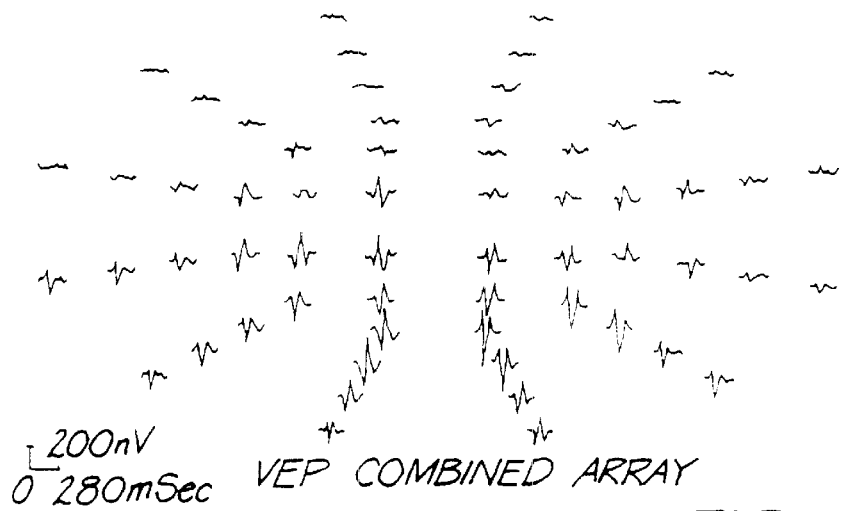
Figure 17F:
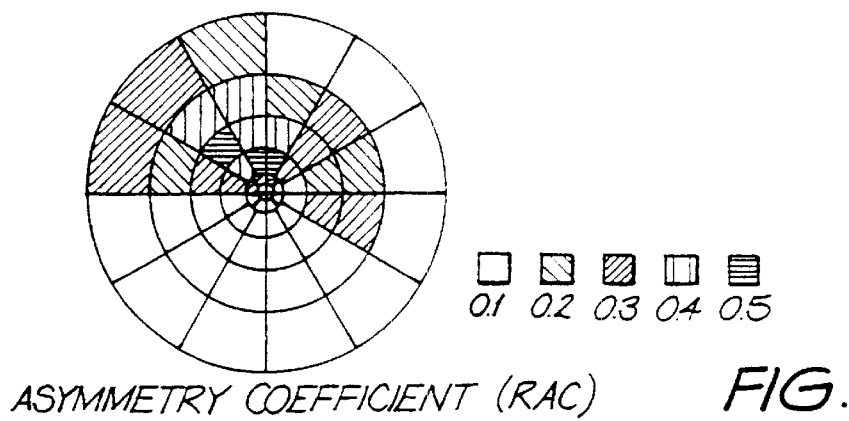
Figure 20A:
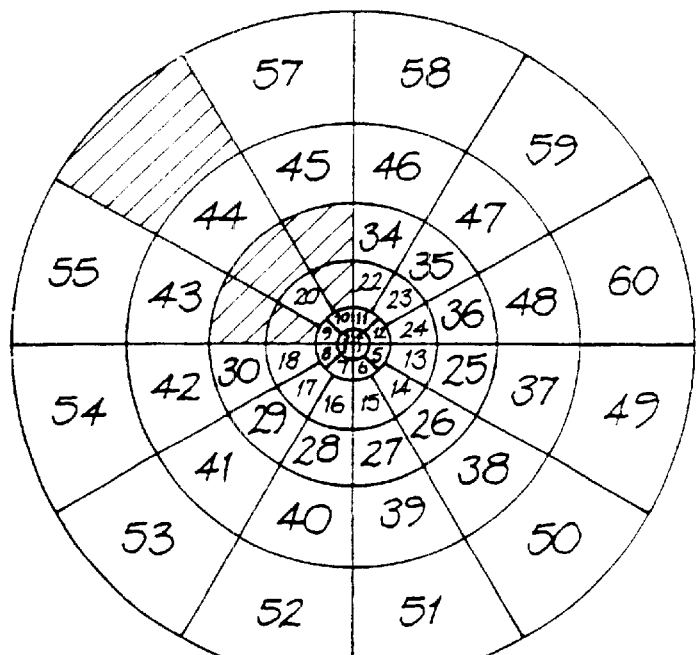
FIGS. 20a and b respectively demonstrate probability plots for non-scaled and scaled values, showing that the scaling algorithm significantly improves detection of the visual field defect relative to normal data base.
Figure 20B:
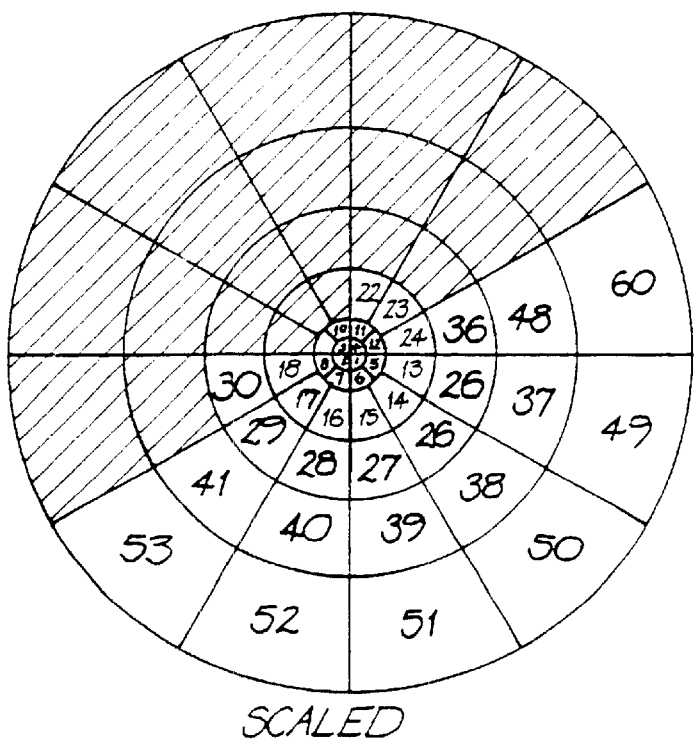
FIGS. 20c and d are the Humphrey visual field and probability plots for the same patient.
Figure 20C:
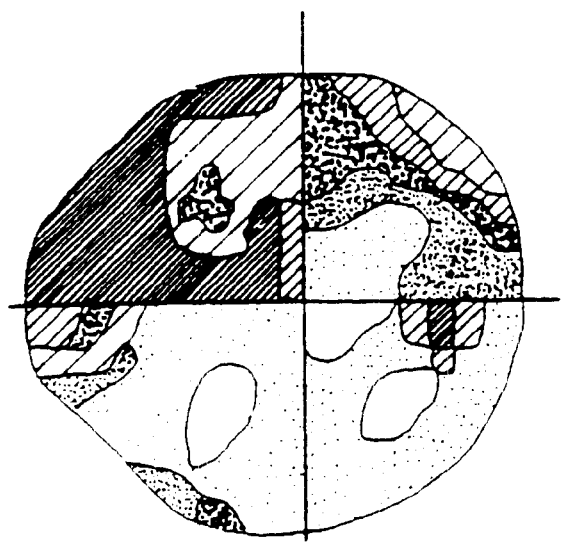
Figure 20D:
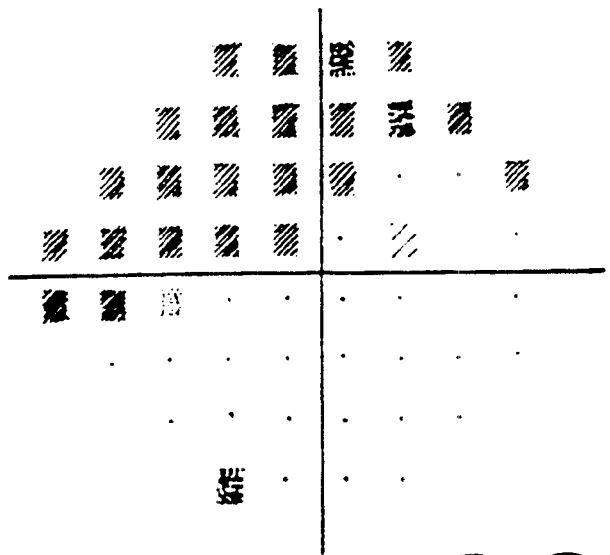

FIG. 16 is an asymmetry analysis of a patient with early glaucoma and an inferior arcuate defect. It is demonstrated that the area of relatively reduced VEP amplitude in the left eye is greater than the corresponding Humphrey visual field defect, indicating involvement of a larger area than suspected on perimetry testing.

FIG. 17 is an asymmetry analysis of a patient with normal tension glaucoma and a superior arcuate defect. It can be seen that the RAC is abnormal not only in upper field of the right eye, but there is also high asymmetry in small paracentral area of the left eye, which on the combined trace array might be accepted as normal. FIG. 18 shows the probability values for the same analysis, confirming that the changes are statistically significant.

Scaling Algorithm

Inter-subject variation of the amplitude of the multi-focal VEP is high. Analysis of data recorded from 35 normal subjects revealed that the inter-subject variation coefficient (ratio of mean amplitude to standard deviation x100) in some segments of the stimulated visual field can be as high as 30–35%. This limits the detection of visual field defects by simple comparison of a particular patient with a normal database. It is especially true in cases where the amplitude of the VEP response is unusually high or low. Individual differences in conductivity of the tissues and skull thickness may account for this variability.

To minimise the effects of inter-subject variability of amplitude, a scaling algorithm has been devised to normalise data, that takes into consideration the responses from both eyes, and thereby compensates for an individual's response characteristics. Rather than scaling responses of one eye based on the overall psychophysical thresholds (as is used in the pattern deviation plot of the Humphrey visual field analysis), scaling is based on the greatest responses from either eye which represent the maximal signal transfer for that subject. The algorithm determines the largest responses within the field of either eye compared to normal values for that particular point. For instance using the tenth largest ratio of amplitude to the normal mean value for the same point using data from both eyes. The amplitudes of all points are then scaled up or down according to the ratio determined. This technique more effectively isolates visual field defects. It is demonstrated in FIGS. 19 and 20. It is recognised that its value clinically will be limited to subjects with two eyes with comparable visual acuity, but this represents the vast majority of early to moderate glaucoma cases.

FIG. 19 shows an example of non-scaled and scaled amplitude values for every segment of the stimulated visual field compared with a normal data base. The bars represent test subject values with the line showing mean normal values. This patient has an unusually high VEP amplitude in healthy areas of the field in both eyes, implying an overall greater signal (see top two graphs). Abnormal areas within the field of the right eye therefore, did not produce statistically significant differences from normals. The scaling procedure however, compensates for the greater overall signal, and more readily identifies abnormal areas. These are seen in the right eye corrected data (lower graph).

FIG. 20 from the same patient shows statistically significant differences ($p<0.05$, shaded areas) in amplitude between the patient and normal data base. Humphrey visual field and probability plots for the same subject are also presented. The scaling algorithm significantly improves detection of the visual field defect relative to the normal data base making it more comparable to the subjective visual scotoma.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of measuring the electrophysiological visual field, comprising the steps of:

placing a pair of electrodes around the inion on the scalp overlying the visual cortex of the brain, in addition to a ground electrode;

visually stimulating an eye; and, recording the data signals picked up by the electrodes.

2. A method according to claim 1, where the signals are used to produce a VEP trace array.

3. A method according to claim 1, where the pair of electrodes are in line with the inion.

4. A method according to claim 3, where the electrodes are placed at equal distances above and below the inion.

5. A method according to claim 4, where the electrodes are placed 2 cm above and 2 cm below the inion.

6. A method according to claim 3, where a first electrode is placed above the inion and another is placed below the inion, and further away from the ion than the first electrode.

7. A method according to claim 3, where an electrode is placed on either side of the inion.

8. A method according to claim 7, where the electrodes are placed 4 cm on either side of the inion.

9. A method according to claim 1, where the pair of electrodes are placed in triangular relationship with the inion.

10. A method according to claim 4, where an electrode is placed to one side of the inion and another below the inion.

11. A method according to claim 10, where the electrode on the side is 4 cm to the right or the left of the inion, and the lower electrode is 4 cm below the inion.

12. An electrode holder in the form of a convex cross, with a fixation strap across the forehead and electrode positions in the positions according to any preceding claim.

13. A method according to claim 1, where one or more additional bipolar electrodes are placed around the inion to record additional channels of data input.

14. A method according to claim 13, where the signals from all channels are used to produce a multi-channel VEP trace array.

15. A method according to claim 1, where a scaling algorithm is employed to normalise data.

16. A method of measuring the electrophysiological visual field, comprising the steps of:

placing a pair of electrodes around the inion on the scalp overlying the visual cortex of the brain, in addition to a ground electrode, where one or more additional bipolar electrodes are placed around the inion to record additional channels of data input, visually stimulating an eye; and, recording the data signals picked up by the electrodes, where the greatest amplitude derived from all recorded channels at each individual point of the visual field is determined, it is then assigned to that point as the optimal signal, and its amplitude used as a measure of response of the visual pathway.

17. A method of measuring the electrophysiological visual field, comprising the steps of:

placing a pair of electrodes around the inion on the scalp overlying the visual cortex of the brain, in addition to a ground electrode;

visually stimulating an eye; and, recording the data signals picked up by the electrodes, where a VEP trace from a particular sector of the combined trace array of one eye is compared to a VEP from the corresponding area of the fellow eye and an amplitude ratio is calculated.

18. A method according to claim 17, where the ratio is then compared to the normal ratio from the corresponding segment of the visual field from a normal data base and a probability of abnormality is calculated.

19. A method of measuring the electrophysiological visual field, comprising the steps of:

placing a pair of electrodes around the inion on the scalp overlying the visual cortex of the brain, in addition to a ground electrode;

visually stimulating an eye; and, recording the data signals picked up by the electrodes, where a scaling algorithm is employed to normalise data, and where the scaling algorithm is based on calculation of the largest responses within the field compared to normal values for that particular point to produce a ratio, and the amplitudes of all points are then scaled up or down according to the ratio determined.

20. A method according to claim 19, where a ratio of amplitude from both eyes to the normal mean value for the same point is used as the ratio.

21. A method according to claim 1, where the electrodes are within 6 cm from the inion.

* * * * *